US011957569B2

(12) United States Patent
Sabater et al.

(10) Patent No.: US 11,957,569 B2
(45) Date of Patent: Apr. 16, 2024

(54) GRAFT TISSUE INJECTOR

(71) Applicants: TissueCor, LLC, Miami, FL (US); University of Miami, Coral Gables, FL (US)

(72) Inventors: Alfonso L. Sabater, Miami, FL (US); Abhishek Shah, Calgary (CA); William B. Buras, Mandeville, LA (US); Alejandro M. Sabater, Miami, FL (US)

(73) Assignees: TissueCor, LLC, Miami, FL (US); University of Miami, Coral Gables, FL (US)

( * ) Notice: Subject to any disclaimer, the term of this patent is extended or adjusted under 35 U.S.C. 154(b) by 692 days.

(21) Appl. No.: 16/804,051

(22) Filed: Feb. 28, 2020

(65) Prior Publication Data
US 2020/0276010 A1 Sep. 3, 2020

Related U.S. Application Data

(60) Provisional application No. 62/812,001, filed on Feb. 28, 2019.

(51) Int. Cl.
*A61M 5/28* (2006.01)
*A61F 2/14* (2006.01)
*A61M 5/315* (2006.01)

(52) U.S. Cl.
CPC ............ *A61F 2/148* (2013.01); *A61F 2/142* (2013.01); *A61M 5/281* (2013.01); *A61M 5/315* (2013.01);
(Continued)

(58) Field of Classification Search
CPC .. A61M 2202/09–097; A61M 2202/10; A61M 3/0279; A61M 5/3134;
(Continued)

(56) References Cited

U.S. PATENT DOCUMENTS 1,704,921 A * 3/1929 Nicoll ................. A61M 5/24
604/232
2,853,070 A * 9/1958 Julliard ............. A61M 5/31586
604/224
(Continued)

FOREIGN PATENT DOCUMENTS

DE 202011106789 U1 11/2011
EP 3162401 A2 5/2017
(Continued)

OTHER PUBLICATIONS

International Search Report, PCT/US2020/020265, issued by European Patent Office, dated Jun. 10, 2020 (4 pages).
(Continued)

*Primary Examiner* — Theodore J Stigell
(74) *Attorney, Agent, or Firm* — Koenig IP Works, PLLC; Katherine Koenig

(57) ABSTRACT

A device and method for aspirating graft tissue and delivering the graft tissue to a target delivery site (for example, when performing Descemet's membrane endothelial keratoplasty). In one embodiment, an injector comprises a cylinder and a plunger at least partially located within the cylinder, the plunger being rotatably advanceable and retractable within the cylinder. In one aspect of the embodiment, rotating the plunger in a first direction within the cylinder controllably aspirates a graft tissue into the injector and rotating the plunger in a second direction opposite the first direction controllably ejects the graft tissue from the injector.

10 Claims, 15 Drawing Sheets

(52) U.S. Cl.
CPC .... *A61M 5/31581* (2013.01); *A61M 5/31596* (2013.01)

(58) Field of Classification Search
CPC .............. A61M 5/315; A61M 5/31511; A61M 5/31581; A61M 2005/3114; A61M 31/007; A61M 2005/341; A61M 5/343; A61M 5/31596; A61M 5/281; A61F 2/148; A61F 2/0095
See application file for complete search history.

(56) References Cited

U.S. PATENT DOCUMENTS

| | | | |
|---|---|---|---|
| 2,903,794 A * | 9/1959 | Carfagni | A61C 5/62 D24/114 |
| 3,738,006 A * | 6/1973 | Lopez | A61C 9/0026 433/80 |
| 4,795,444 A * | 1/1989 | Hasegawa | A61M 5/3129 604/218 |
| 5,336,088 A * | 8/1994 | Discko, Jr. | A61C 5/66 433/90 |
| 5,722,971 A | 3/1998 | Peyman | |
| 5,964,748 A | 10/1999 | Peyman | |
| 6,019,765 A * | 2/2000 | Thornhill | A61F 2/4601 606/93 |
| 6,203,538 B1 | 3/2001 | Peyman | |
| 6,217,571 B1 | 4/2001 | Peyman | |
| 6,221,067 B1 | 4/2001 | Peyman | |
| 6,280,470 B1 | 8/2001 | Peyman | |
| 8,029,515 B2 | 10/2011 | Shiuey | |
| 8,673,002 B2 | 3/2014 | Walter et al. | |
| 9,326,847 B2 * | 5/2016 | Sanger | A61F 2/1672 |
| 9,999,497 B2 | 6/2018 | Shiuey | |
| 10,041,865 B2 | 8/2018 | Tran | |
| 10,085,887 B2 | 10/2018 | Donitzky et al. | |
| 10,130,511 B2 | 11/2018 | Dantus | |
| 11,311,680 B2 | 4/2022 | Okihara | |
| 2001/0027314 A1 | 10/2001 | Peyman | |
| 2004/0122438 A1 * | 6/2004 | Abrams | A61B 17/8816 606/93 |
| 2008/0281341 A1 | 11/2008 | Miller et al. | |
| 2009/0069817 A1 | 3/2009 | Peyman | |
| 2010/0057093 A1 * | 3/2010 | Ide | A61F 2/148 606/107 |
| 2010/0069915 A1 | 3/2010 | Shiuey | |
| 2010/0211051 A1 | 8/2010 | Weston et al. | |
| 2012/0059488 A1 | 3/2012 | Shimmura | |
| 2012/0123533 A1 | 5/2012 | Shiuey | |
| 2012/0226286 A1 | 9/2012 | Weston et al. | |
| 2013/0085567 A1 | 4/2013 | Tan et al. | |
| 2013/0274875 A1 | 10/2013 | Ide et al. | |
| 2013/0317605 A1 | 11/2013 | Ide et al. | |
| 2013/0331870 A1 | 12/2013 | Hargis | |
| 2014/0221822 A1 | 8/2014 | Ehlers et al. | |
| 2014/0288643 A1 | 9/2014 | Torres et al. | |
| 2015/0297340 A1 * | 10/2015 | Esguerra | A61F 2/148 606/107 |
| 2016/0270904 A1 | 9/2016 | Neusidl | |
| 2017/0079838 A1 | 3/2017 | Nishida et al. | |
| 2017/0128263 A1 | 5/2017 | Maminishkis | |
| 2017/0258633 A1 | 9/2017 | Vure et al. | |
| 2017/0340428 A1 | 11/2017 | Szurmann et al. | |
| 2018/0106704 A1 | 4/2018 | Tran | |
| 2018/0143109 A1 | 5/2018 | Tran | |
| 2018/0220884 A1 | 8/2018 | Joo et al. | |
| 2018/0263756 A1 | 9/2018 | Shiuey | |
| 2018/0311027 A1 | 11/2018 | Distefano | |
| 2019/0038400 A1 | 2/2019 | Samudre | |
| 2019/0060054 A1 | 2/2019 | Balachandran | |
| 2019/0125520 A1 | 5/2019 | Bachmann et al. | |
| 2019/0159931 A1 | 5/2019 | Balachandran | |
| 2019/0223997 A1 | 7/2019 | Nun et al. | |
| 2019/0224002 A1 | 7/2019 | Springer et al. | |
| 2019/0269826 A1 | 9/2019 | Peyman | |
| 2019/0380870 A1 | 12/2019 | Lue et al. | |
| 2020/0015959 A1 | 1/2020 | Wensrich et al. | |
| 2021/0069426 A1 | 3/2021 | Huculak et al. | |
| 2021/0244530 A1 | 8/2021 | El-Ayari et al. | |
| 2022/0176043 A1 | 6/2022 | Wang | |
| 2023/0014433 A1 | 1/2023 | Abdullayev et al. | |

FOREIGN PATENT DOCUMENTS

| | | | |
|---|---|---|---|
| EP | 3698758 A1 | 8/2020 | |
| FR | 2720279 | * 12/1995 | |
| FR | 2720279 A1 | 12/1995 | |
| WO | 2009132212 A2 | 10/2009 | |
| WO | 2011102725 A1 | 8/2011 | |
| WO | 2011126144 A1 | 10/2011 | |
| WO | 2012065602 A2 | 5/2012 | |
| WO | WO-2012065602 A2 * | 5/2012 | A61F 2/148 |
| WO | 2013011185 A1 | 1/2013 | |
| WO | 2013059813 A1 | 4/2013 | |
| WO | 2014179698 A3 | 11/2014 | |
| WO | 2016094387 A3 | 6/2016 | |
| WO | 2020176818 A1 | 9/2020 | |
| WO | 2021108257 | 1/2022 | |

OTHER PUBLICATIONS

International Search Report for copending PCT/IB2022/058183, dated Mar. 2, 2023 (6 pages).

* cited by examiner

GRAFT TISSUE INJECTOR

CROSS-REFERENCE TO RELATED APPLICATIONS

This application is related to and claims priority to U.S. Provisional Patent Application No. 62/812,001, filed Feb. 28, 2019, entitled GRAFT TISSUE INJECTOR, the entirety of which is incorporated herein by reference.

GOVERNMENT RIGHTS STATEMENT

None.

TECHNICAL FIELD

This disclosure relates generally to a device and method for aspirating graft tissue and delivering the graft tissue to a target delivery site, such as within an anterior chamber of an eye.

BACKGROUND

Corneal transplants or grafts are the most common and successful transplantation procedures in medicine. In fact, more than 280,000 donor corneas are recovered every year and at least 180,000 corneal transplants are performed annually worldwide. According to a global survey that was conducted between 2012 and 2013, around 40% of the corneas were recovered in the United States.

The cornea is the clear, protective outer layer of the eye, and consists primarily of three layers, namely, the corneal epithelium (outer layer), the corneal stroma, and the corneal endothelium (inner layer). Each layer has different characteristics. For example, the corneal epithelium is a thin multicellular epithelial tissue layer of fast-growing and easily regenerated cells. The corneal stroma is a thick transparent middle layer that includes regularly arranged collagen fibers and keratocytes, which are the cells that help maintain the structure of the corneal stroma. The corneal stroma consists of approximately 200 layers of mainly type I and type V collagen fibers. Up to 90% of the corneal thickness is composed of stroma.

Finally, the corneal endothelium is a monolayer of mitochondria-rich cells. These cells are responsible for regulating fluid and solute transport between the aqueous humor and corneal stroma. Unlike the corneal epithelium, endothelial cells do not regenerate. Instead, they stretch to compensate for dead cells, which reduces the overall cell density of the endothelium, which affects fluid regulation. If endothelial cells can no longer maintain a proper fluid balance, stromal swelling due to excess fluids and subsequent loss of transparency will occur, which may cause corneal edema.

Fuchs' endothelial dystrophy and pseudophakic bullous keratopathy (PBK) are two of the most frequent indications for corneal transplantation. Until a few years ago, full thickness corneal transplantation was the only available treatment for endothelial layer replacement. However, although this procedure is able to restore corneal endothelial function, it has several drawbacks, such as high post-operative astigmatism, risk of tissue dehiscence and risk of infections and tissue rejection.

In the 1960s, a method of endothelial keratoplasty (EK) using an anterior approach via a laser-assisted in situ keratomileusis (LASIK) flap was described, and in 1999, a technique for posterior lamellar keratoplasty was developed. In a procedure called posterior lamellar keratoplasty (PLK), the posterior lamella, Descemet's membrane, and endothelium was dissected through a 9-mm sclerocorneal incision. A donor button consisting of posterior stroma, Descemet's membrane, and endothelium was then inserted and held in place by an air bubble while the patient lay supine.

In the 1990s, as the PLK procedure was further modified and a procedure called deep lamellar endothelial keratoplasty (DLEK) was developed. DLEK eliminated surface corneal sutures and incisions, leading to faster visual rehabilitation. However, DLEK requires the manual lamellar dissection of the deep corneal stroma from both donor and recipient, which is considered by surgeons to be difficult and laborious.

This consequently led to the development of Descemet's stripping endothelial keratoplasty (DSEK). DSEK has the advantages of being easier for the surgeon to perform and of providing a smoother interface on the recipient side for the visual axis. Preparation of the donor tissue in endothelial keratoplasty has also been made easier with the utilization of an automated microkeratome. The addition of this component to the surgical procedure has been popularized as Descemet's stripping automated endothelial keratoplasty (DSAEK).

Descemet's membrane endothelial keratoplasty (DMEK) is a partial-thickness cornea transplant procedure that involves a selective transplantation of a monolayer of donor endothelial cells and Descemet's membrane in the absence of a stromal tissue carrier. While the idea of DMEK was first introduced in 1998, the first successful report of DMEK did not occur until 2006.

In the DMEK technique, the donor corneoscleral rim is positioned with the endothelial side up. The scleral spur and Descemet's membrane are separated for 360 degrees, after which a superficial trephination of approximately 9 mm is made in the posterior stroma. The donor corneoscleral rim is submerged under Optisol or balanced saline solution (BSS) to decrease the surface tension and lower the risk of a potential Descemet's membrane tear. The endothelium is stripped from the posterior donor stroma with nontoothed forceps, creating a circular sheet of Descemet's membrane with an endothelial monolayer of cells. Owing to the elastic properties of the Descemet's membrane, a "Descemet's roll" forms spontaneously after the circular layer of endothelium/Descemet's membrane is removed from the donor posterior stroma, with the endothelium on the outside of the roll. The roll of tissue is stained with 0.06% trypan blue. The tissue is next placed in a tissue injector. Next, a scleral or corneal incision is made. With a reverse Sinskey hook, a circular portion of Descemet's membrane is scored and stripped from the recipient posterior stroma, completing a 9.0-mm diameter "descemetorhexis." The stripped Descemet's membrane and endothelium are removed from the eye. Using the injector, the donor tissue roll is inserted into the anterior chamber and the graft is oriented endothelial side down by indirect manipulation of the tissue with air and/or fluid. While maintaining the anterior chamber with fluid and air, the graft is gently spread out over the iris. Then, an air bubble is injected underneath the donor Descemet's membrane to position the tissue onto the recipient posterior stroma. The anterior chamber is completely filled with air for 30 to 60 minutes followed by an air-liquid exchange to pressurize the eye.

Loading of the tissue into the injector and inserting the tissue into the anterior chamber are two of the most important steps in the DMEK procedure. Loading of the tissue requires controlled vacuum to draw the tissue towards the injector. Some injectors require the tissue to be loaded through the injection end, which is narrow and makes the aspiration more difficult and traumatic. For this reason, new injectors allow the tissue to be loaded through the connection part of the injector, which has a larger diameter and makes the aspiration easier and less traumatic for the tissue. However, these types of injectors require extra tubing to aspirate the tissue, as the syringe cannot be adapted to the connection part of the injector. Additionally, aspiration of the tissue requires vacuum, which sometimes is difficult to control and causes the tissue to be aspirated too rapidly or to slowly. This can cause the tissue to hit the walls of the injector, potentially causing endothelial cell loss.

On the other hand, insertion of the tissue into the anterior chamber is performed by pressing the plunger of a syringe preloaded with BSS. Unfortunately, pressure cannot be accurately controlled and the tissue is often injected too rapidly into the anterior chamber and hits the anterior chamber angle, which can cause endothelial cell loss. Additionally, to minimize the induced astigmatism caused by the incision and to improve chamber stability, new injectors have a smaller diameter that can go through small incisions of approximately 2.5 mm. However, this smaller injector diameter causes more friction against the tissue and may also cause endothelial cell loss during tissue insertion.

SUMMARY

Some embodiments advantageously provide a device, system, and method for aspirating graft tissue and delivering the graft tissue to a target delivery site. In one non-limiting example, the device and method may be used to deliver graft tissue to a location within an anterior chamber of an eye when performing Descemet's membrane endothelial keratoplasty. In one embodiment, an injector comprises: a cylinder; and a plunger at least partially located within the cylinder, the plunger being rotatably advanceable within the cylinder and one of rotatably retractable and linearly retractable within the cylinder.

In one aspect of the embodiment, the plunger is rotatably retractable within the cylinder, rotating the plunger in a first direction within the cylinder is configured to controllably aspirate a graft tissue into the injector and rotating the plunger in a second direction opposite the first direction is configured to controllably eject the graft tissue from the injector. In one aspect of the embodiment, the plunger includes: a shaft having a first portion and a second portion opposite the first portion, the second portion having a free end; and a knob coupled to the first portion, an outer surface of at least a portion of the first portion defining threading. In one aspect of the embodiment, the cylinder includes a body having an inner surface, at least a portion of the inner surface defining threading that is complementary to the threading of the first portion of the outer surface of the shaft of the plunger.

In one aspect of the embodiment, the plunger is linearly retractable within the cylinder. In one aspect of the embodiment, the cylinder includes an inner surface, at least a portion of the inner surface having an interrupted threading with a threaded portion and a non-threaded portion extending longitudinally through the threaded portion; and the plunger includes a shaft having a follower, the follower being configured to travel within the threaded portion when the plunger is rotatably advanced and being configured to travel within the non-threaded portion when the plunger is linearly retracted.

In one aspect of the embodiment, the cylinder includes a body having: a first opening; a second opening opposite the first opening; and a chamber, the chamber being in fluid communication with the first opening and the second opening. In one aspect of the embodiment, the cylinder further includes an end wall at least partially defining the second opening and a connection extension, the connection extension having: a first end meeting the end wall; a second end opposite the first end, the second end defining an opening; and a lumen, the lumen being in fluid communication with the second opening of the body and the second opening of the connection extension. In one aspect of the embodiment, the body has a first longitudinal axis and the connection extension has a second longitudinal axis that is different than the first longitudinal axis, the second longitudinal axis being oriented at an angle from the first longitudinal axis.

In one aspect of the embodiment, the angle is less than approximately 90°.

In one aspect of the embodiment, the second longitudinal axis is oriented at an angle from the first longitudinal axis, the angle being between approximately 22.5° and approximately 67.5°.

In one aspect of the embodiment, the injector further comprises a tissue cartridge including: a first portion defining a first opening and having a first outer diameter, the first opening having a first diameter; a second portion opposite the first portion and defining a second opening, the second portion having a second outer diameter that is less than the first outer diameter of the first portion and the second opening having a second diameter that is less than the first diameter of the first opening; and a chamber, the chamber being in fluid communication with the first opening of the tissue cartridge and the second opening of the tissue cartridge. In one aspect of the embodiment, the connection extension has an outer diameter that is slightly smaller than the first diameter of the first opening of the tissue cartridge, such that the connection extension is removably insertable within the first opening of the tissue cartridge and securable therein by friction fit; and the connection extension has an inner diameter that is slightly larger than the outer diameter of the second portion of the tissue cartridge, such that the second portion of the tissue cartridge is removably insertable within the connection extension and securable therein by friction fit.

In one aspect of the embodiment, the tissue cartridge further includes an inner surface and an outer surface, at least a portion of at least one of the inner surface and the outer surface being coated with at least one layer of a nano-ceramic material.

In one embodiment, a kit for corneal transplant comprises: an injector including: a cylinder, the cylinder having a bent configuration; and a plunger at least partially insertable into the cylinder, the plunger being rotatably advanceable within the cylinder and at least one of rotatably and linearly retractable within the cylinder; and a container including a tissue cartridge with a graft tissue therein, the tissue cartridge including a first portion with a first opening and a second portion with a second opening opposite the first opening, the tissue cartridge being reversibly couplable to the cylinder of the injector. In one aspect of the embodiment, the container further includes: a reservoir portion; a lid; a latch mechanism configured to couple the reservoir portion and lid; and a chamber defined between the reservoir portion and the lid, the chamber being sized and configured to contain the tissue cartridge. In one aspect of the embodiment, the container further includes: at least one first positioning element coupled to the lid and extending in a first direction; at least one second positioning element coupled to the reservoir portion and extending in a second direction opposite the first direction; and at least one containment element, the at least one first positioning element and the at least one second positioning element being configured to retain the tissue cartridge therebetween and the at least one containment element being configured to at least partially obstructing the first opening of the tissue cartridge when the lid is coupled to the reservoir portion and the tissue cartridge is within the chamber. In one aspect of the embodiment, the cylinder has a connection extension, the cylinder having a first longitudinal axis and the connection extension having a second longitudinal axis that is different than the first longitudinal axis, the second longitudinal axis being oriented relative to the first longitudinal axis by an angle of between approximately 22.5° and approximately 67.5°.

In one embodiment, a method of delivering corneal graft tissue to a delivery site comprises: inserting a connection extension of a cylinder of an injector into a first opening of a first portion of a tissue cartridge, the cylinder having a body with a first longitudinal axis, the connection extension extending from the body and having a second longitudinal axis that is different than the first longitudinal axis, an inner surface of the cylinder having a first threading; inserting a second portion of the tissue cartridge having a second opening through an incision and into an anterior chamber of a patient's eye, the second portion of the tissue cartridge having an outer diameter that is smaller than an outer diameter of the first portion of the tissue cartridge; and rotating a plunger in a first direction within the cylinder to advance a shaft of the plunger within the cylinder to inject the graft tissue into the anterior chamber of the patient's eye through the second opening of the tissue cartridge, the shaft of the plunger having a second threading that is complementary to and engages the first threading. In one aspect of the embodiment, the method further comprising, before the step of inserting a connection extension of a cylinder of an injector into a first opening of a first portion of a tissue cartridge: inserting the second portion of the tissue cartridge within an opening of the connection extension; positioning the first opening of the tissue cartridge proximate the graft tissue; rotating the plunger in a second direction opposite the first direction within the cylinder to retract the shaft of the plunger within the cylinder to aspirate the graft tissue into the tissue cartridge through the first opening of the tissue cartridge.

BRIEF DESCRIPTION OF THE DRAWINGS

A more complete understanding of embodiments described herein, and the attendant advantages and features thereof, will be more readily understood by reference to the following detailed description when considered in conjunction with the accompanying drawings wherein.

DETAILED DESCRIPTION

Figure 1:
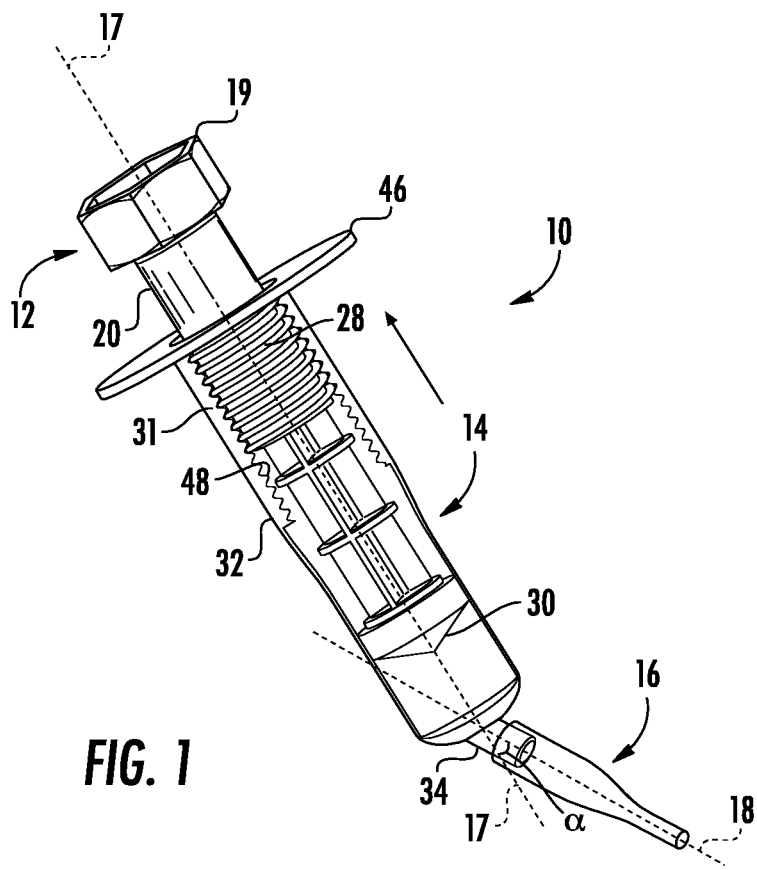
FIG. 1 shows an exemplary embodiment of a graft tissue injector having a plunger and a tissue cartridge in accordance with the present disclosure, the plunger being in a first position and the tissue cartridge being in an injection configuration.

Before describing in detail exemplary embodiments, it is noted that the embodiments reside primarily in combinations of apparatus components and steps related to aspirating graft tissue into an injector and delivering (injector or ejecting) the graft tissue to a delivery location. Accordingly, the system and method components have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

As used herein, relational terms, such as "first" and "second," "top" and "bottom," and the like, may be used solely to distinguish one entity or element from another entity or element without necessarily requiring or implying any physical or logical relationship or order between such entities or elements. The terminology used herein is for the purpose of describing particular embodiments only and is not intended to be limiting of the concepts described herein. As used herein, the singular forms "a", "an" and "the" are intended to include the plural forms as well, unless the context clearly indicates otherwise. It will be further understood that the terms "comprises," "comprising," "includes" and/or "including" when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

The terms "corneal transplant" and "corneal graft" are used interchangeably herein to refer to a medical procedure, and the term "corneal graft tissue" is used herein to refer to the tissue used for the medical procedure of corneal transplant or corneal graft.

Figure 2:
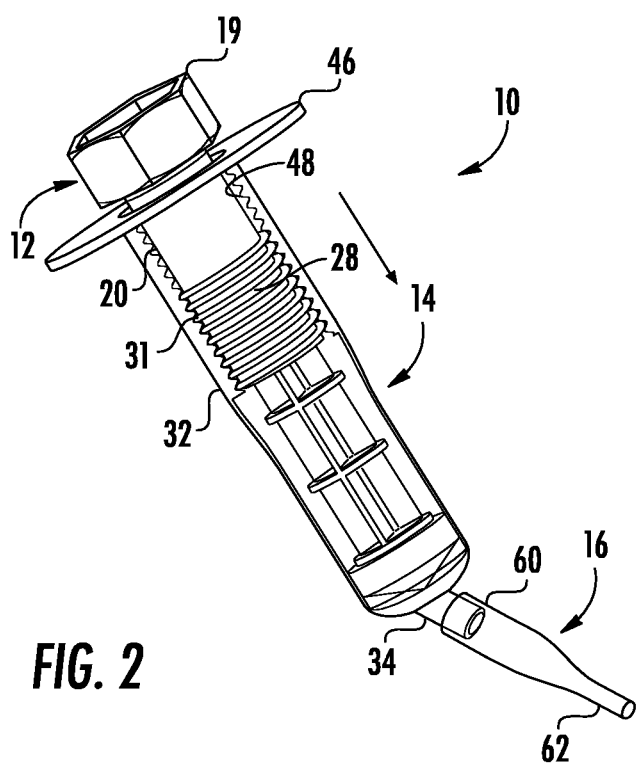
FIG. 2 shows the graft tissue injector of FIG. 1, the plunger being in a second position and the tissue cartridge being in the injection configuration in accordance with the present disclosure.
Figure 3:
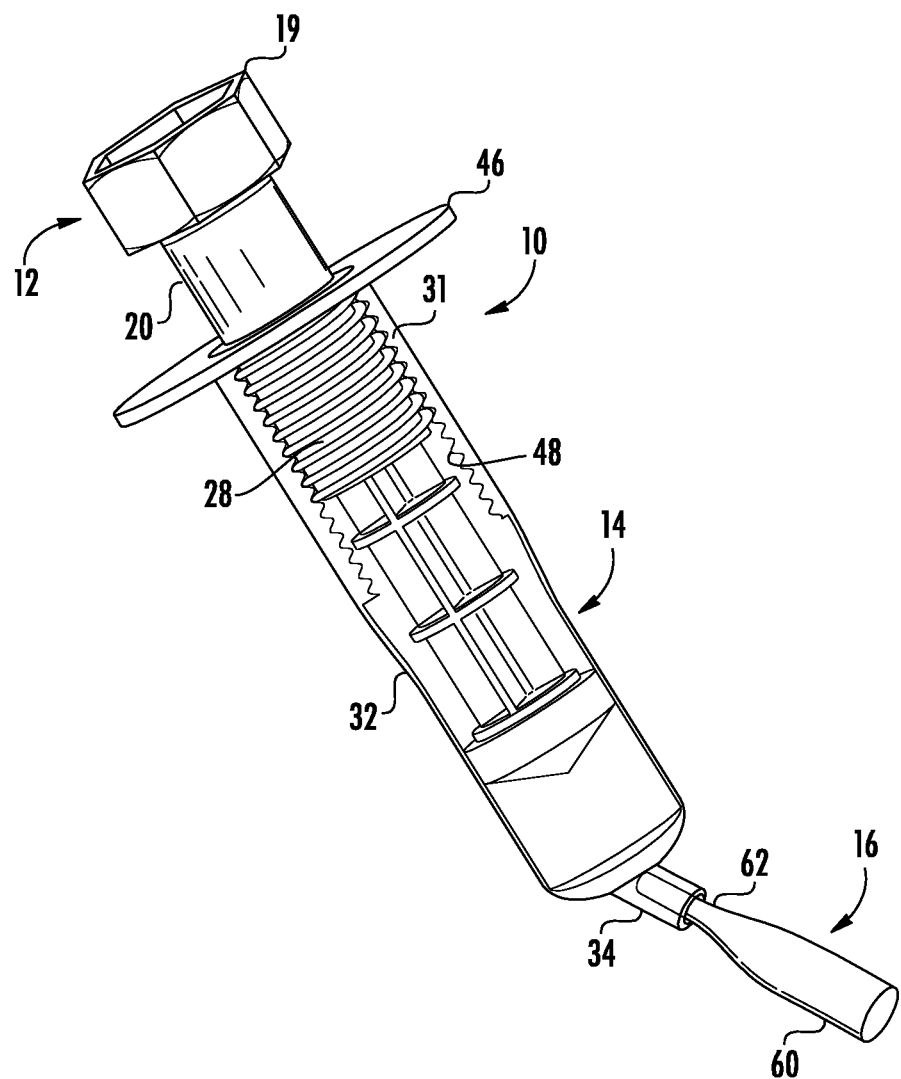
FIG. 3 shows the graft tissue injector of FIG. 1, the tissue cartridge being in an aspiration configuration in accordance with the present disclosure.

Referring now to the figures in which like reference designators are used for like elements, a graft tissue injector 10 (also referred to herein as an injector 10) is shown in FIGS. 1-3. FIGS. 1 and 2 show the injector 10 in an injection configuration (or second configuration, when the injector 10 is in use) and FIG. 3 shows the injector 10 in an aspiration configuration (or first configuration, when the injector 10 is in use). The injector 10 is configured for use in a medical procedure, such as in a Descemet's membrane endothelial keratoplasty (DMEK). In one embodiment, the corneal tissue injector is configured to aspirate a rolled piece of donor corneal tissue (referred to herein as "graft tissue"), including at least a portion of an endothelium and a Descemet's membrane, into the injector 10 for subsequent injection into an anterior chamber of a patient's eye (the aqueous humor-filled space inside the eye between the iris and the corneal endothelium).

Generally referring to the figures, in some embodiments the injector 10 generally includes a plunger 12, a cylinder 14, and includes or is configured to include a tissue cartridge 16 that is removably couplable to the cylinder 14. When the injector 10 is assembled, the injector 10 has a bent shape, with a first portion having a first longitudinal axis 17 and a second portion having a second longitudinal axis 18 that is different than the first longitudinal axis 17. In one embodiment, the first portion includes the plunger 12 and at least a portion of the cylinder 14 and the second portion includes at least a portion of the cylinder 14 and the tissue cartridge 16 (for example, as shown in FIG. 1). To use the injector 10, the user engages with the plunger 12 to retract the plunger 12 a distance within the cylinder 14, thereby aspirating a graft tissue into the injector 10. Conversely, to inject the graft tissue from the injector 10 into or at a delivery site, the user engages with the plunger 12 to advance the plunger 12 in an opposite direction a distance within the cylinder 14, thereby ejecting the graft tissue from the injector 10. Additionally, as is discussed in greater detail below, in one embodiment the tissue cartridge 16 is in a first position when graft tissue is aspirated into the graft tissue injector 10 (for example, as shown in FIG. 3) and the tissue cartridge 16 is in a second position when graft tissue is injected from the graft tissue injector 10 (for example, as shown in FIG. 2).

Referring now generally to FIGS. 1-5, the injector 10 generally includes a threaded plunger 12 and a threaded cylinder 14. In one exemplary method of use, to aspirate graft tissue into the injector 10, the plunger 12 is turned or rotated in a first direction (for example, counter-clockwise) to draw the plunger 12 within the cylinder 14 and away from the tissue cartridge 16 (for example, in the direction indicated by the arrow in FIG. 1). Conversely, to inject the graft tissue from the injector 10 into or at a delivery site, the plunger 12 is turned in a second direction opposite the first direction (for example, clockwise) to advance the plunger 12 within the cylinder 14 toward the tissue cartridge 16 (for example, in the direction indicated by the arrow in FIG. 2).

Figure 4:
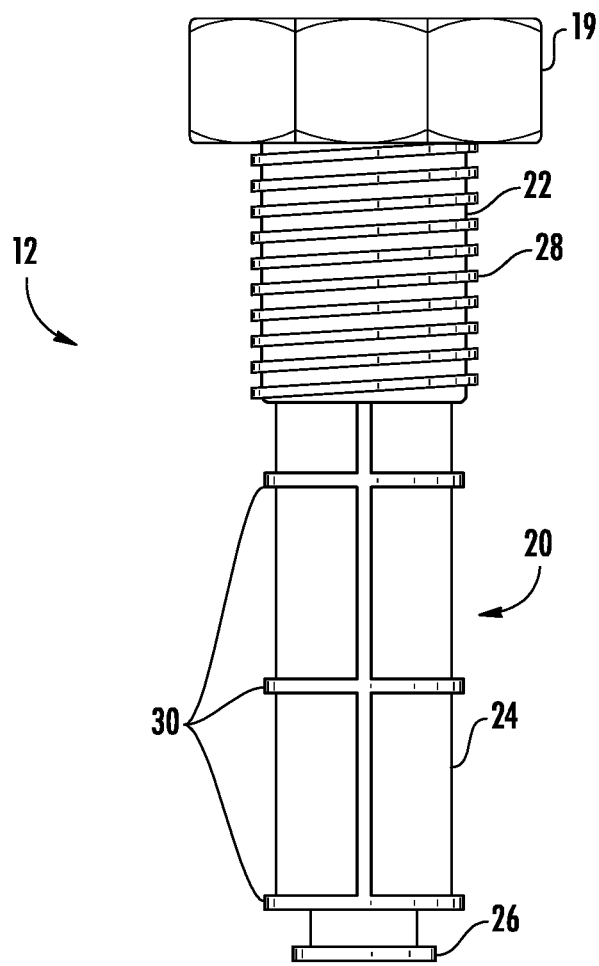
FIG. 4 shows an exemplary embodiment of the plunger for a graft tissue injector, for example, a graft tissue injector of FIG. 1, in accordance with the present disclosure.

Referring now to FIG. 4, the plunger 12 is shown in greater detail. In one embodiment, the rotating plunger 12 has an elongated shape and generally includes a knob 19 and a shaft 20. In one embodiment, the knob 19 is polygonal in cross section, but it will be understood that the knob 19 may have any suitable size, shape, and/or configuration that is easily graspable by the user. In one embodiment, the shaft 20 has an elongated shape and includes a first portion 22 coupled to, fused with, or extending from the knob 19 and a second portion 24 opposite the first portion 22, the second portion 24 including a free end 26. At least a portion of the shaft 20 is threaded. In one embodiment, an outer surface of the first portion 22 of the shaft 20 includes a continuous threading 28 extending from the knob 19 to a location between the first portion 22 and the second portion 24 of the shaft 20. In one embodiment, the lower edge of the continuous threading 28 defines the boundary between the first portion 22 and the second portion 24. However, it will be understood that the continuous threading may extend over the shaft 20 in any suitable location and/or over any suitable distance. As used herein, the term "continuous threading" refers to a threading pattern that extends around the shaft 20 at least once, or at least 360°, without break or interruption. Optionally, the shaft 20 may also include one or more areas, such as at or proximate the free end 26, that include a material 30 such as rubber or a similar material, or simply protrusions from and formed of the same material as the shaft 20, that enhances contact between the shaft 20 and an inner surface 31 of the cylinder 14. This may prevent leaks and thereby help force liquid, and the graft tissue, from the injector 10 when the plunger 12 is rotated to advance the shaft 20 of the plunger 12 within the cylinder 14. Further, in some embodiments the free end 26 includes or is coupled to an end piece of material 30, which may be composed of, for example, rubber or a similar material. In some embodiments, the free end 26 is co-molded or formed with an integrated stopper that is composed of the same or different material than the shaft 20. In some embodiments, the stopper is an end piece of material 30 that is affixed, adhered, or otherwise coupled to the free end 26.

Figure 5:
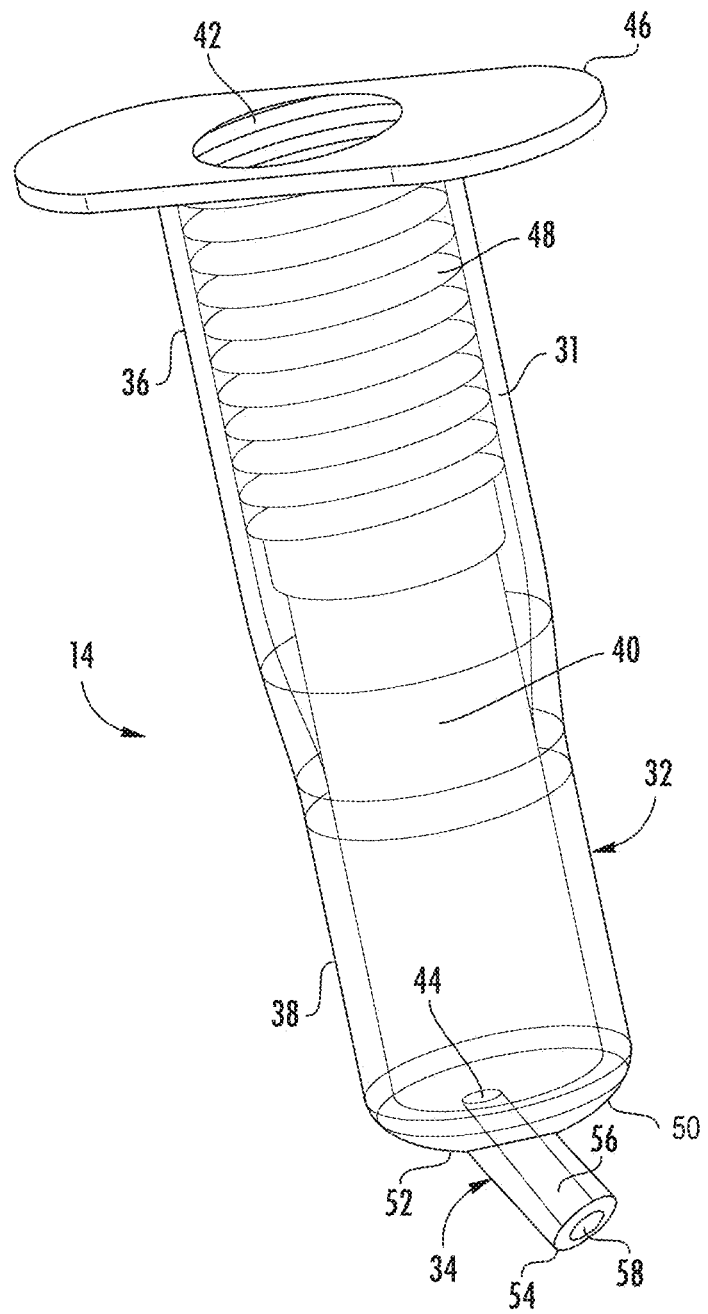
FIG. 5 shows an exemplary embodiment of a cylinder of the graft tissue injector of FIG. 1 in accordance with the present disclosure.

Referring now to FIG. 5, the cylinder 14 is shown in greater detail. In one embodiment, the cylinder 14 includes a body 32 and a connection extension 34 that is coupled to or extends from one end of the body 32. In one embodiment, the body 32 has an elongated (and, in one embodiment, tubular or at least substantially tubular) shape and generally includes a first end 36, a second end 38 opposite the first end 36, and a chamber 40 therebetween. The chamber 40 is at least partially defined by the inner surface 31 of the body 32.

Figure 6:
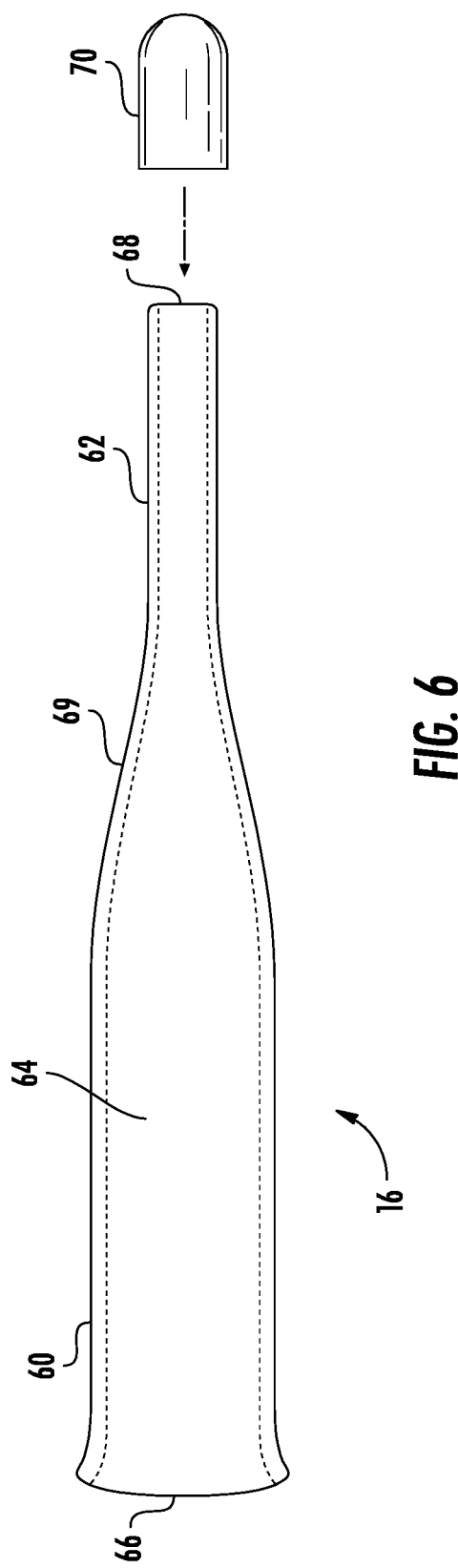
FIG. 6 shows an exemplary embodiment of a tissue cartridge for the graft tissue injector in accordance with the present disclosure.
Figure 7:
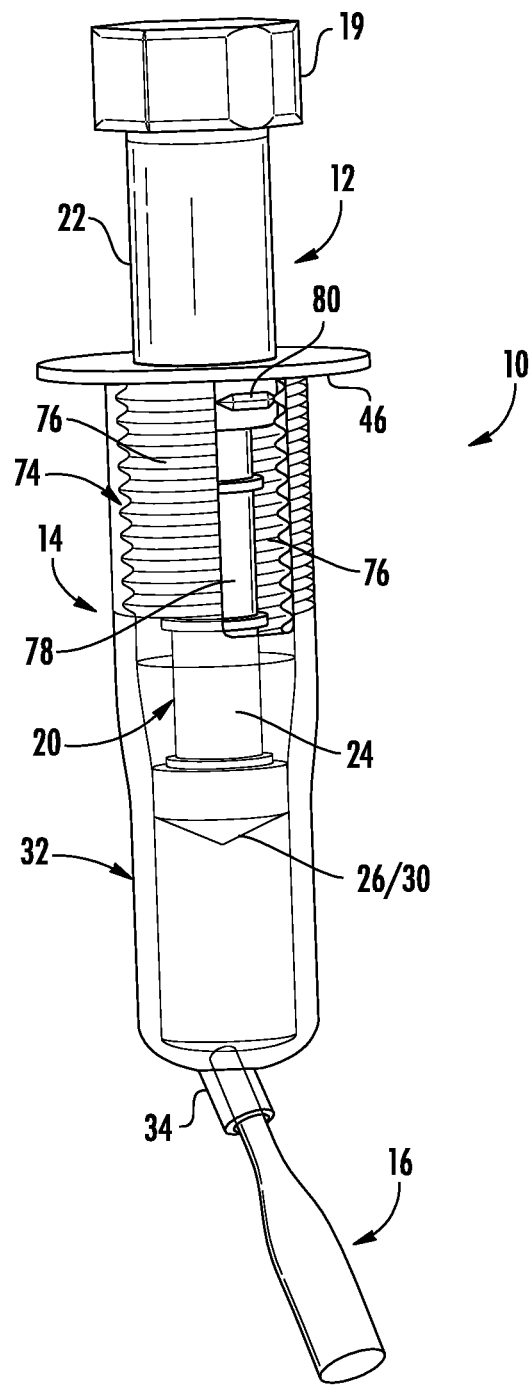
FIG. 7 shows an exemplary embodiment of a graft tissue injector having a plunger and a tissue cartridge in accordance with the present disclosure, the plunger being in a first position and the tissue cartridge being in an aspiration configuration.

Continuing to refer to FIG. 5, in one embodiment the first end 36 of the body 32 defines a first opening 42 and the second end 38 of the body 32 defines a second opening 44, and the first opening 42 has a larger inner diameter than the second opening 44. The first opening 42 and the second opening 44 are each in fluid communication with the chamber 40. In some embodiments, the body 32 has a continuous, or at least substantially continuous, outer diameter and/or inner diameter along its entire length. In one non-limiting example, the chamber 40 has a continuous, or at least substantially continuous, diameter (that is, the body 32 has a continuous, or at least substantially continuous, inner diameter) along its length that is the same as, or at least substantially the same as, the inner diameter of the first opening 42. In other embodiments, the body 32 has a varying outer and/or inner diameter. In one non-limiting example, a portion of the body 32 proximate the first end 36 has a larger outer diameter and a larger inner diameter than a portion of the body 32 proximate the second end 38 (for example, as shown in FIGS. 5-7). In some embodiments, the cylinder 14 includes a finger grip or flange 46 extending from the first end 36 of the body and extending at least partially around the first opening 42.

Continuing to refer to FIG. 5, in one embodiment the first opening 42 and at least a portion of the chamber 40 (for example, a portion of the chamber 40 that is proximate the first end 36 of the body 32) is sized and configured to receive at least a portion of the shaft 20 of the plunger 12 in close tolerance, such that fluid does not escape the injector 10 when the shaft 20 is rotated or advanced within the body 32. Additionally, at least a portion of the body 32 includes threading 48 within the chamber 40, on the inner surface 31 of the body 32. In one embodiment, the body 32 includes threading 48 within the chamber 40 on the inner surface extending from the first opening 42 toward the second opening 44 and over a distance that is equal to, or at least substantially equal to (for example, within ±3 mm) the distance over which the first portion 22 of the shaft 20 of the plunger 12 is threaded. Further, the number of times the threading 28, 48 passes around 360° of the outer surface of the shaft 20 and the inner surface of the body 32, respectively, depends on the characteristics of the threading 48, such as pitch, size, thread angle, and the like. However, it will be understood that the threaded distances of the shaft 20 and the inner surface of the body 32 may be the same or different. The threading 48 in the chamber 40 is sized and configured to rotatably engage with the continuous threading 28 on the shaft 20 of the plunger 12. Put another way, the threading of 28 of the shaft 20 is complementary to and engageable with the threading 48 in the chamber 40. Thus, the shaft 20 of the plunger 12 may be screwed into, and rotatably movable within (that is, advanceable and retractable along the first longitudinal axis 17 of the cylinder 14), at least a portion of the chamber 40 of the body 32.

Continuing to refer to FIG. 5, in one embodiment the connection extension 34 is coupled to or extends from the second end 38 of the body 32. In one embodiment, the second end 38 of the body 32 includes an end wall 50 that surrounds or defines the second opening 44. In one embodiment, the connection extension 34 extends from the end wall 50 at an acute angle to define the second longitudinal axis 18 of the injector 10. In one embodiment, the connection extension 34 generally has a tubular shape, with a first end 52, a second end 54 opposite the first end 52, and a lumen 56 therebetween. The second end 54 defines an opening 58 in fluid communication with the lumen 56. As shown in FIG. 5, in one embodiment the first end 52 of the connection extension 34 is coupled to or meets the end wall 50 of the body 32 such that the second opening 44 of the body 32 (and, therefore, the chamber 40) is in fluid communication with the lumen 56 and the opening 58 of the connection extension 34.

Continuing to refer to FIG. 5, in one embodiment the connection extension 34 has an outer diameter that is less than at least the diameter of the end wall 50. Likewise, in one embodiment the lumen 56 of the connection extension 34 has a diameter that is less than the diameter of the chamber 40 within at least a portion of the body 32 (that is, the connection extension 34 has an inner diameter that is less than the inner diameter of at least a portion of the body 32). Further, as is shown in FIG. 5, the connection extension 34 is canted relative to the body 32. Put another way, the body 32 has a first longitudinal axis that is the same as, or at least substantially the same as, the first longitudinal axis 17 of the first portion of the injector 10 and the connection extension 34 has a second longitudinal axis that is the same as, or at least substantially the same as, the second longitudinal axis 18 of the second portion of the injector 10 (for example, as shown in FIG. 1). In one embodiment, the first and second longitudinal axes 17, 18 intersect at an angle α of less than approximately 90° (±5°). In one embodiment, the angle α is between approximately 22.5° and approximately 67.5° (±5°). Thus, the injector 10 may be referred to as having a bent configuration, and this configuration may facilitate handling during both aspiration of the graft tissue and insertion of the graft tissue into the delivery site, such as the anterior chamber of the patient's eye. When the tissue cartridge 16 is coupled to the connection extension 34, the tissue cartridge 16 lies along the same longitudinal axis as the tissue cartridge 16 (i.e. the second longitudinal axis 18). Likewise, although axes 17, 18 are not shown in FIGS. 3 and 5, it will be understood that the injector 10 has the same bent configuration regardless of how the tissue cartridge 16 is coupled to the connection extension 34 (or whether a tissue cartridge 16 is coupled to the connection extension 34).

Continuing to refer to FIG. 5, in one embodiment, the connection extension 34 and the body 32 are formed as a single, unitary piece. In another embodiment, the connection extension 34 is rigidly or flexibly coupled to the end wall 50 of the body 32. In one embodiment the body 32 and the connection extension 34 are composed of the same material. For example, the entire cylinder 14 may be composed of a rigid material that is transparent and/or translucent, such as glass, plastic, or polymer. Thus, the connection extension 34 may be rigidly connected to or extend from the end wall 50 of the body 32 and, therefore, tissue cartridge 16 may be at a fixed position relative to the body 32 when connected to the connection extension 34. In another embodiment, the body 32 and the connection extension 34 are composed of different materials. In one non-limiting example, the body 32 may be composed of a rigid first material (that is either opaque or transparent and/or translucent), such as glass, plastic, or polymer, whereas the connection extension 34 may be composed of a second material (that is either opaque or transparent and/or translucent) that is more flexible than, or that has a durometer that is less than, the material from which the body 32 is composed. This may allow some flexibility in the second portion of the injector 10 when in use. Put another way, when connected to the connection extension 34, the tissue cartridge 16 may be at least somewhat movable relative to the body 32.

Figure 8:
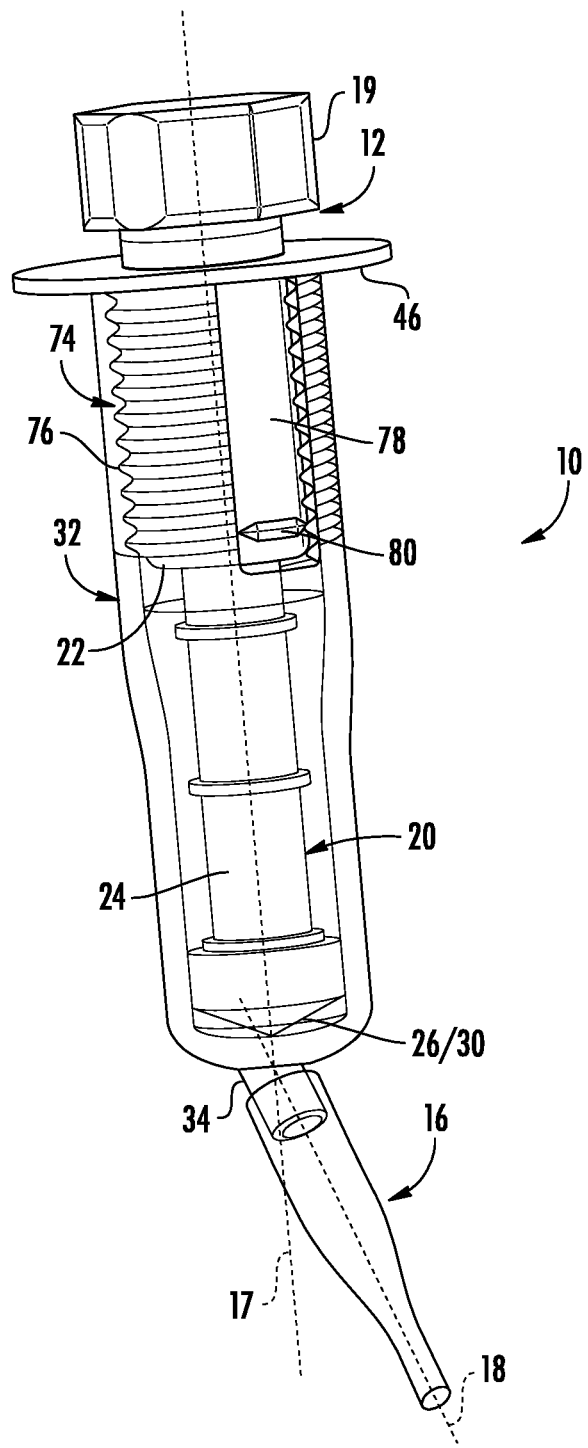
FIG. 8 shows the graft tissue injector of FIG. 7, the plunger being in a second position and the tissue cartridge being in the injection configuration in accordance with the present disclosure.

Referring now to FIG. 6, the tissue cartridge 16 is shown in greater detail. In one embodiment, the tissue cartridge 16 generally has an elongated shape (and, in some embodiments, has a flute shape, as shown in FIG. 8) and includes a first portion 60, a second portion 62 opposite the first portion 60, and a chamber 64 therebetween. The chamber 64 is defined by an inner surface of the tissue cartridge 16. In one embodiment, the first portion 60 defines a first opening 66 and the second portion 62 defines a second opening 68, and the first and second openings 66, 68 are each in fluid communication with the chamber 64. In one embodiment, the first opening 66 has a larger diameter than the second opening 68. Further, in one embodiment the first portion 60 has a first outer diameter and the second portion 62 has a second outer diameter that is less than the first outer diameter. The tissue cartridge 16 may also include a transition portion 69 between the first and second portions 60, 62 that has varying outer diameters between the first and second outer diameters. Likewise, in one embodiment the chamber 64 within the first portion 60 has a first diameter and the second portion 62 has a second diameter that is less than the first diameter (that is, the first portion 60 of the tissue cartridge 16 has an inner diameter that is greater than greater than the inner diameter of the second portion of the tissue cartridge 16). The chamber 64 within the transition portion 69 may also have varying diameters between the diameters of the first and second portions 60, 62 (that is, the transition portion 69 of the tissue cartridge 16 may have a varying inner diameter, or plurality of inner diameters, between the inner diameters of the first and second portions 60, 62). Put another way, in one embodiment the tissue cartridge 16 and chamber 64 therein have a tapered shape, and the second portion of the tissue cartridge may be an elongate tube of reduced diameter that is sized and configured to be at least partially inserted through a corneoscleral incision for injection and placement of the graft tissue within the anterior chamber of the patient's eye. Further, in some embodiments, the second portion 62 of the tissue cartridge 16 may have a blunt shape where the second portion 62 defines the second opening 68 (for example, as shown in FIG. 6), and in other embodiments the second portion 62 has a beveled shape where the second portion 62 defines the second opening 68 (for example, as shown in FIGS. 7 and 8).

Continuing to refer to FIG. 6, in one embodiment, the first portion 60 has a slight flute or flange shape surrounding the first opening 66. Further, in one embodiment the first opening 66 of the tissue cartridge 16 and at least a portion of the chamber 64 (for example, the portion of the chamber 64 within the first portion 60 of the tissue cartridge 16) is sized and configured to fit over at least the second end 54 of the connection extension 34 of the cylinder 14, such that the tissue cartridge 16 may be secured to the cylinder 14 by a friction fit and the chamber 64 of the tissue cartridge 16 is in fluid communication with the lumen 56 of the connection extension 34 and, therefore, the chamber 40 of the body 32. Put another way, the inner diameter of the first opening 66 and at least a portion of the chamber 64 is slightly larger than the outer diameter of at least the second end 54 of the connection extension 34 such that the tissue cartridge 16 may be secured coupled to and removed from the connection extension 34 by hand. Further, in one embodiment the outer diameter of the second portion 62 of the tissue cartridge 16 is sized and configured to fit within the opening 58 of the connection extension 34 of the cylinder 14, such that the tissue cartridge 16 may be secured to the cylinder 14 by a friction fit and the chamber 64 of the tissue cartridge 16 is in fluid communication with the lumen 56 of the connection extension 34 and, therefore, the chamber 40 of the body 32. Put another way, the inner diameter of the opening 58 is slightly larger than the outer diameter of second portion 62 of the tissue cartridge 16. As is described in greater detail below, in one embodiment the second portion 62 of the tissue cartridge 16 is engaged with the connection extension 34 when aspirating fluid and graft tissue (as shown in FIG. 3), and the first portion 60 of the tissue cartridge is engaged with the connection extension 34 when injecting fluid and graft tissue (as shown in FIGS. 1 and 2). Additionally, an inner and/or outer surface of the connection extension 34 and an inner and/or outer surface of the tissue cartridge 16 may optionally be mateably threaded so the tissue cartridge 16 may be screwed onto or into the connection extension 34. Further, in some embodiments, the injector 10 further includes a cap 70 that is removably coupled or couplable to the second end 62 of the tissue cartridge 16 to prevent graft tissue from escaping the chamber 64 through the second opening 68 once the injector 10 has been used to aspirate graft tissue and/or for pre-loaded tissue cartridges 16A, as discussed in greater detail below.

Continuing to refer to FIG. 6, in one embodiment the tissue cartridge 16 is composed of a rigid material that is transparent and/or translucent, such as glass, plastic, or polymer. For example, in one embodiment the tissue cartridge 16 is composed of a clear polymer. This allows the tissue cartridge 16 to have the same inner diameter(s), but smaller outer diameter(s), than commercially known tissue cartridges composed of glass because certain polymers are more flexible and resistant to breakage than glass. Additionally, at least the portion of the second portion 62 surrounding the second opening 68 may be rounded or blunted to create an atraumatic tip. Alternatively, the portion of the second portion 62 surrounding the second opening may be beveled or include a bevel, which may facilitate insertion of the tissue cartridge into the eye. Thus, the tissue cartridge 16 of the present disclosure may be not only less traumatic when used to inject a tissue graft because of its reduced outer diameter(s) (at least the outer diameter of the second portion 62) and/or rounded tip, which allows for a smaller incision, but also more break-resistant than tissue cartridges 16 composed of glass. Further, in one embodiment at least a portion of the tissue cartridge 16 is coated with at least one layer of a lubricious material that lowers the coefficient of friction of that portion of the tissue cartridge 16, such as polytetrafluoroethylene (PTFE), a nano-ceramic, or the like. In one embodiment, the lubricious material has a coefficient of friction of between approximately 0.1 and approximately 0.5 (±0.1). For example, a nano-ceramic coating that has a coefficient of friction that is at least 50% less than glass may be used on the inner surface and/or the outer surface of the tissue cartridge 16, which reduces the likelihood of damage of the tissue graft and the patient's tissue during insertion. In one embodiment, both the inner surface (within the chamber 64) and the outer surface of the second portion 62 of the tissue cartridge 16 may be coated with at least one layer of a lubricous material or combination of lubricous materials.

Figure 9:
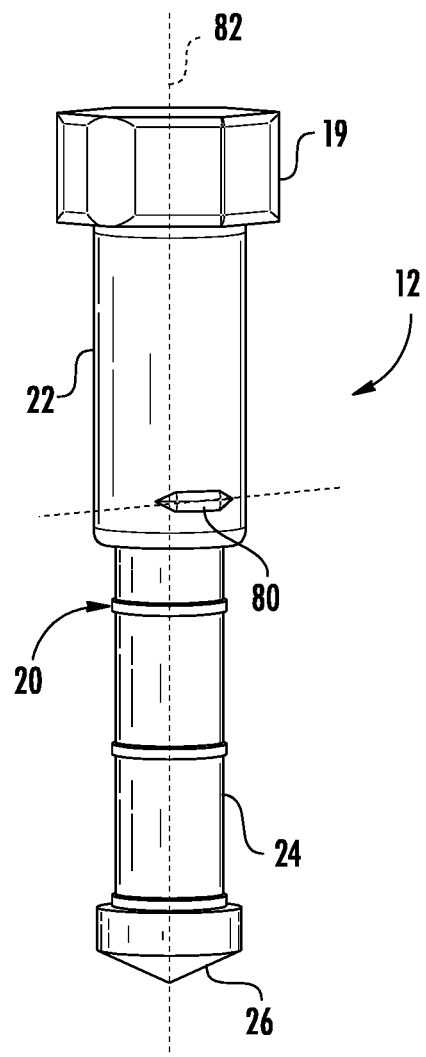
FIG. 9 shows an exemplary embodiment of a plunger for a graft tissue injector, for example, a graft tissue injector of FIG. 7, in accordance with the present disclosure.

Referring now to FIGS. 7-9, a further embodiment of a graft tissue injector 10 is shown (also referred to as injector 10). Unless otherwise noted, and where indicated by a common reference number, the components of the injector 10 in some embodiments are the same as are as described above regarding the injector 10 of FIGS. 1-5 and will therefore not be discussed here for the sake of brevity. FIG. 7 shows a side view of an exemplary injector 10 in an aspiration configuration; FIG. 8 shows a side view of the injector 10 in an injection configuration; and FIG. 9 shows an exemplary plunger 12 of the injector 10 in greater detail.

Referring now to FIGS. 7 and 8, the injector 10 has the same bent configuration as the injector 10 of FIGS. 1-3, and generally includes a cylinder 14 with a connection extension 34 and includes or is configured to include a tissue cartridge 16 that is removably couplable to the cylinder 14. Further, the tissue cartridge 16 is removably couplable to the cylinder 14 in an aspiration configuration (as shown in FIG. 7) or an injection configuration (as shown in FIG. 8), as shown and described above regarding FIGS. 1-6.

Continuing to refer to FIGS. 7 and 8, the body 32 of the cylinder 14 includes a threading that is different than the threading 48 of the injector 10 of FIGS. 1-3. The threading shown in FIGS. 7 and 8 is an interrupted threading 74 wherein the threaded track extends around only a portion (that is, less than the entire circumference or less than 360°) of the inner surface 31 of the cylinder 14. The interrupted threading 74 thus defines a threaded portion 76 and an interrupted, non-threaded portion 78. The non-threaded portion 78 has a width that is less than the diameter of the chamber 40 and extends longitudinally along at least a portion of the inner surface and, in some embodiments, passes through an entirety of the length of the interrupted threading 74.

Referring now to FIG. 9, the plunger 12 is shown in greater detail. Unless otherwise noted, and where indicated by a common reference number, the components of the plunger 12 of FIG. 9 are in some embodiments are the same as the plunger 12 of FIG. 4 and will therefore not be discussed here for the sake of brevity. In one embodiment, the first portion 22 is not threaded, but does include a follower 80 that protrudes from a surface of the first portion 22 of the shaft 20, as shown in FIG. 9. The follower 80 is sized and configured to not only travel within the channels of the threaded portion 76, but also to pass through the non-threaded portion 78. In one non-limiting example, the follower 80 has a width that is less than the width of the non-threaded portion 78, and is oriented at non-orthogonal angle to the longitudinal axis 82 of the shaft 20. For example, the follower 80 may be oriented such that it can pass through the channels of the threaded portion 76. Further, in some embodiments, the follower 80 may be sized and oriented such that the plunger 12 may be used with the cylinder 14 of the injector 10 of FIGS. 1-5 (that is, the follower 80 may be sized and configured to pass within the tracks of the continuous threading 48).

Continuing to refer to FIG. 9, in one exemplary method of use, the user draws the plunger 12 through the chamber 40 in a direction away from the tissue cartridge 16 to aspirate the graft tissue. For example, the user aligns the follower 80 with the non-threaded portion 78 and draws the plunger 12 longitudinally (that is, linearly along the first longitudinal axis 17 of the cylinder 14 without rotation) through the chamber 40 with the follower 80 passing through the non-threaded portion 78 and toward the first opening 42 of the body 32. Following the non-threaded portion 78 allows the user to retract the plunger 12, and thereby aspirate the graft tissue, faster than if the plunger 12 were rotated through the interrupted threading 74. Further, in one exemplary method of use, the user rotates the plunger 12 through the channels of the threaded portion 76 in a direction toward the tissue cartridge 16 to controllably inject or deliver the graft tissue to the delivery site. For example, the user aligns the follower 80 with the channels of the threaded portion 76 and rotates the plunger 12 (for example, in the clockwise direction) to advance the plunger 12 through the chamber 40 with the follower 80 passing through the threaded portion 76 and toward the tissue cartridge 16. Following the threaded portion 76 allows the user to advance the plunger 12, and thereby inject the graft tissue, more slowly and in a more controlled manner than if the plunger 12 were rapidly advanced through the chamber 40 with the follower 80 in the non-threaded portion 78 of the interrupted threading 74.

Figure 10:
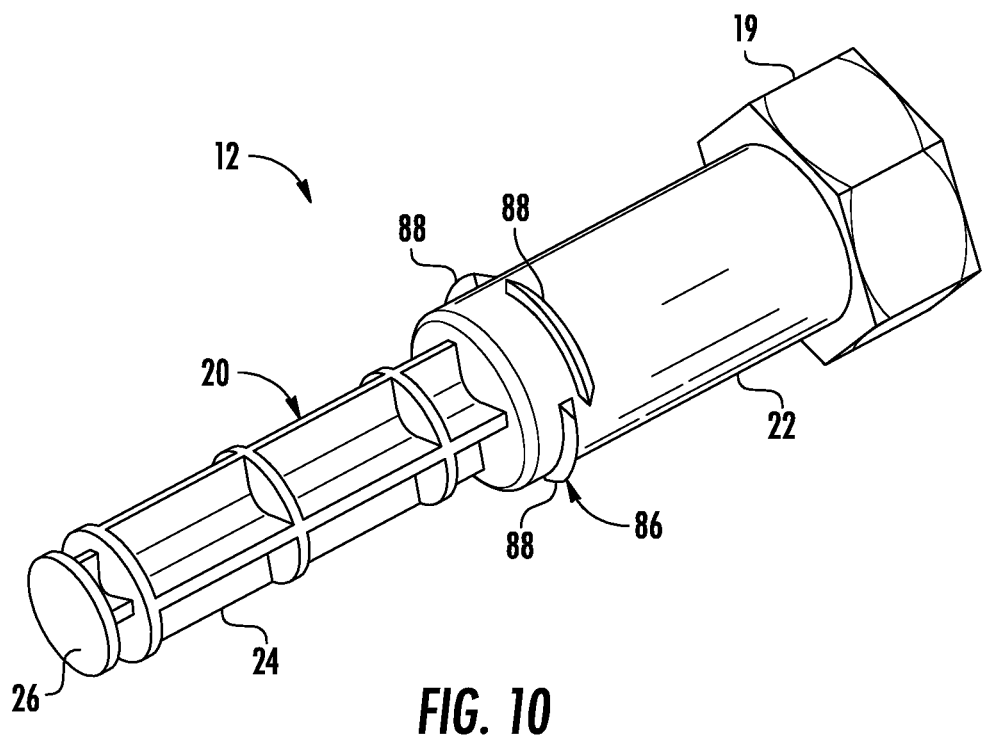
FIG. 10 shows a further exemplary embodiment of a plunger for a graft tissue injector, for example, a graft tissue injector of FIG. 1 in accordance with the present disclosure.

Referring now to FIG. 10, a further exemplary embodiment of a plunger 12 is shown. Unless otherwise noted, and where indicated by a common reference number, the components of the plunger 12 of FIG. 10 in some embodiments are the same as are as described above regarding the plungers 12 of FIGS. 4 and 9 and will therefore not be discussed here for the sake of brevity. In one embodiment, the plunger 12 of FIG. 10 is substantially the same as the plunger 12 of FIG. 4 and/or FIG. 9, except the plunger 12 of FIG. 10 does not include the continuous threading 28 as in FIG. 4 or the follower 80 as in FIG. 9. Instead, in some embodiments the plunger 12 of FIG. 10 includes an engagement element 86 that extend around the outer surface of the first portion 22 of the shaft 20 by approximately one rotation (that is, approximately 360°±20°). In one non-limiting example, the engagement element 86 includes a plurality of spaced-apart elongated tabs or protrusions 88 that are aligned in approximately one threading rotation, to create a minimal threading pattern. Thus, in some embodiments the plunger 12 is configured to be used with the continuous threading 48 of the cylinder 14 of FIGS. 1-5 (that is, the protrusions 88 of the engagement element 86 are configured to matingly engage the continuous threading 48 of the cylinder 14). In some embodiments, the plunger 12 is also configured to be used with the interrupted threading 74 of the cylinder 14 of FIGS. 7 and 8; however, each protrusion 88 may have a length that is greater than the width of the non-threaded portion 78 of the interrupted threading 74 and, therefore, the plunger 12 could not be freely drawn longitudinally through the chamber 40. The engagement element 86 may result in the plunger 12 being easier to manufacture than, for example, the continuous threading 28 of the plunger 12 and may also reduce the precision required when matching the continuous threading 28 of the plunger 12 with the continuous threading 48 of the cylinder 14.

Figure 11:
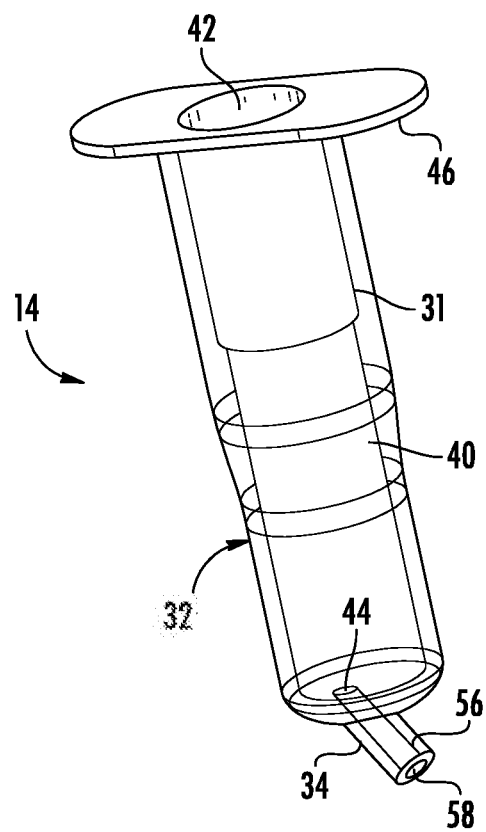
FIG. 11 shows a further exemplary embodiment of a cylinder of a graft tissue injector in accordance with the present disclosure.

Referring now to FIG. 11, a further exemplary embodiment of a cylinder 14 for an injector 10 is shown. Unless otherwise noted, and where indicated by a common reference number, the components of the cylinder 14 of FIG. 11 are in some embodiments the same as are as described above and will therefore not be discussed here for the sake of brevity. For example, in one embodiment, the external appearance of the cylinder 14 of FIGS. 1-5 and the cylinder 14 of FIGS. 7 and 8. However, unlike the cylinder 14 embodiments discussed above, in one embodiment the cylinder 14 of FIG. 11 includes an inner surface 31 that is free of threading or other structural features for engagement with the plunger 12. Thus, any of the plungers discussed herein and/or other plungers may be used with the cylinder 14 of FIG. 11. To accommodate this, the diameter of the chamber 40, at least within the portion of the body 32 proximate the first end 36, may be somewhat larger than the diameter of the chamber 40 of the cylinder of FIG. 1-5 or 7 or 8, while still allowing a fit between the body 32 and at least a portion of the plunger in close tolerance to prevent the leakage of fluid. In one non-limiting example, the plunger may include an end piece of material 30 that is wide enough to contact the inner surface 31 of the cylinder 14.

Figure 12:
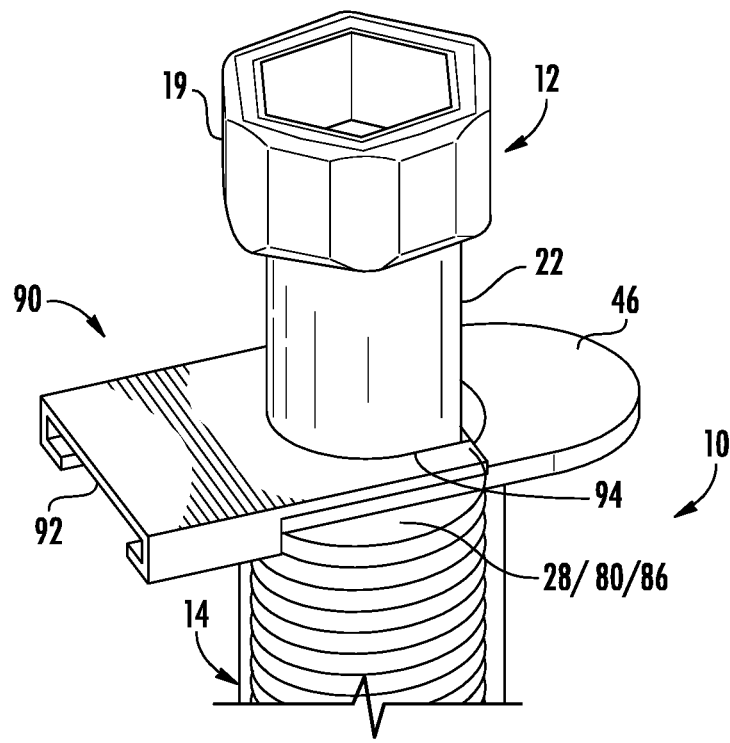
FIG. 12 shows an exemplary embodiment of a retainment element for use with a graft tissue injector in accordance with the present disclosure.

Referring now to FIG. 12, a retainment element 90 is shown. In one embodiment, the retainment element 90 is includes a sleeve portion 92 at a first end and a collar portion 94 at a second end opposite the first end. In one embodiment, the sleeve portion 92 is sized and configured to receive at least a portion of the flange 46 of the body 32 and the collar portion 94 is configured to receive a portion of the shaft 20 of the plunger 12. Further, in one embodiment, the sleeve portion 92 is configured such that the sleeve portion 92 may be slid over and entrap at least a portion of the flange 46, thereby preventing movement of the sleeve portion 92 and, therefore, the retainment element 90 in a direction parallel to the longitudinal axis 17 of the cylinder 14. That is, the retainment element 90 is passed over the flange 46 in a direction that is orthogonal to the longitudinal axis 17 of the cylinder. Further, as the sleeve portion 92 is slid over the flange 46, the collar portion 94 at least partially surrounds the shaft 20 of the plunger. In some embodiments, the plunger 12 includes threading, a follower, an engagement element, or other structural feature protruding from the shaft 20. However, in some embodiments the collar portion 94 defines an opening or cut out that is sized to fit in close tolerance with the shaft 20, or is at least smaller than the overall diameter of the shaft 20, including the structure feature(s). Therefore, when the retainment element 90 is coupled to the cylinder 14 and the structural feature(s) of the shaft 20 are positioned within the chamber 40 of the cylinder 14, the structural feature(s) cannot pass through the collar portion 94 and the retainment element 90 prevents the plunger 12 from retracting out of the cylinder 14.

Thus, it will be appreciated that various combinations of cylinder 14 and plunger 12 are contemplated. For example, in some embodiments the injector 10 includes a cylinder 14 and a plunger 12. In one embodiment, the cylinder 14 includes an inner surface 31 having continuous threading 28 and this cylinder 14 is configured to be used with any of the following plungers 12: (1) a plunger 12 having complementary continuous threading 48 on at least a portion of the shaft 20; (2) a plunger 12 that is not threaded but includes a follower 80 on the shaft 20 that is sized and configured to travel within the continuous threading 28 within the cylinder 14; (3) a plunger 12 that includes an engagement element 86 that circumscribes the shaft 20 of the plunger 12 approximately once (for example, 360°±20°), the engagement element 86 including a plurality of protrusions 88 from the shaft 20 and being sized and configured to travel within the continuous threading 28 within the cylinder 14; and (4) a plunger without threading or other engagement feature. In one embodiment, the cylinder includes an inner surface 31 that has an interrupted threading 74, the interrupted threading 74 including a threaded portion 76 and a non-threaded portion 78, and this cylinder 14 is configured to be used with any of the following plungers 12: (1) a plunger 12 having complementary continuous threading 48 on at least a portion of the shaft 20; (2) a plunger 12 that is not threaded but includes a follower 80 on the shaft 20 that is sized and configured to travel within the threaded portion 76 and to move longitudinally through the non-threaded portion 78; (3) a plunger 12 that includes an engagement element 86 that circumscribes the shaft 20 of the plunger 12 approximately once (for example, 360°±20°), the engagement element 86 including a plurality of protrusions 88 from the shaft 20 and being sized and configured to travel within the continuous threading 28 within the cylinder 14; and (4) a plunger without threading or other engagement feature. In one embodiment, the cylinder has an inner surface 31 that is free of threading or other structural feature protruding from or into the inner surface 31 and this cylinder 14 is configured to be used with any of the following plungers 12: (1) a plunger 12 having complementary continuous threading 48 on at least a portion of the shaft 20; (2) a plunger 12 that is not threaded but includes a follower 80 on the shaft 20 that is sized and configured to travel within the threaded portion 76 and to move longitudinally through the non-threaded portion 78; (3) a plunger 12 that includes an engagement element 86 that circumscribes the shaft 20 of the plunger 12 approximately once (for example, 360°±20°), the engagement element 86 including a plurality of protrusions 88 from the shaft 20 and being sized and configured to travel within the continuous threading 28 within the cylinder 14; and (4) a plunger without threading or other engagement feature. Further, it will be understood that any of these combinations may include a retainment element 90.

It will be further appreciated that more than one injector 10 may be used during a given procedure or series of procedures. For example, a user may use both a first injector 10 having a cylinder 14 without threading (as in FIG. 11) to aspirate graft tissue into the tissue cartridge 16 (as the plunger may be rapidly withdrawn through the cylinder 14 to quickly aspirate the graft tissue) and a second injector 10 having a cylinder 14 and plunger 12 combination that is usable to controllably inject the graft tissue from the tissue cartridge 16 into the delivery site (for example, as shown in FIGS. 1-5 and/or FIGS. 7-10). In one non-limiting example, the user may aspirate the graft tissue using the first injector 10 (with the second portion 62 of the tissue cartridge 16 coupled to the connection extension 34), remove the tissue cartridge 16 from the first injector 10 and then secure the cap 70 to the tissue cartridge 16 to obstruct or cover the second opening 68, and then connect the first portion 60 of the tissue cartridge 16 to the connection extension 34. Once the user is ready to begin the graft tissue delivery procedure, the user may the remove the cap 70 from the tissue cartridge 16. However, it will be understood that the user may use a single injector 10 or any combination of multiple injectors 10 and/or combinations of cylinder(s) 14 and plunger(s) 12, depending on the type of procedure, time between aspiration and delivery of graft tissue, user preference, or the like.

Figure 13:
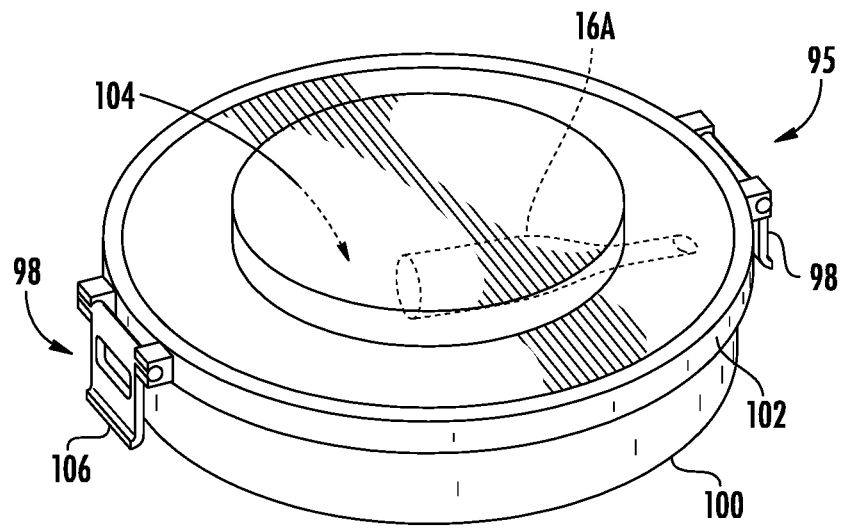
FIG. 13 shows an exemplary embodiment of a container for a tissue cartridge in accordance with the present disclosure.
Figure 14:
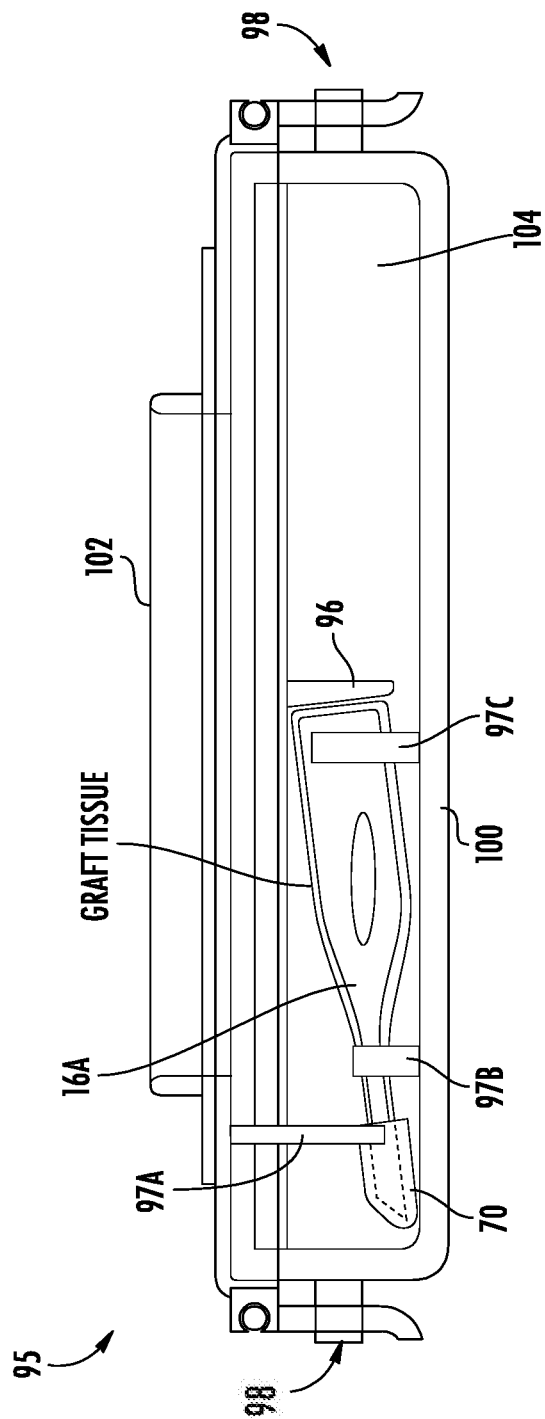
FIG. 14 shows a side view of the container and positioning elements and a tissue cartridge therein, in accordance with the present disclosure.
Figure 15:
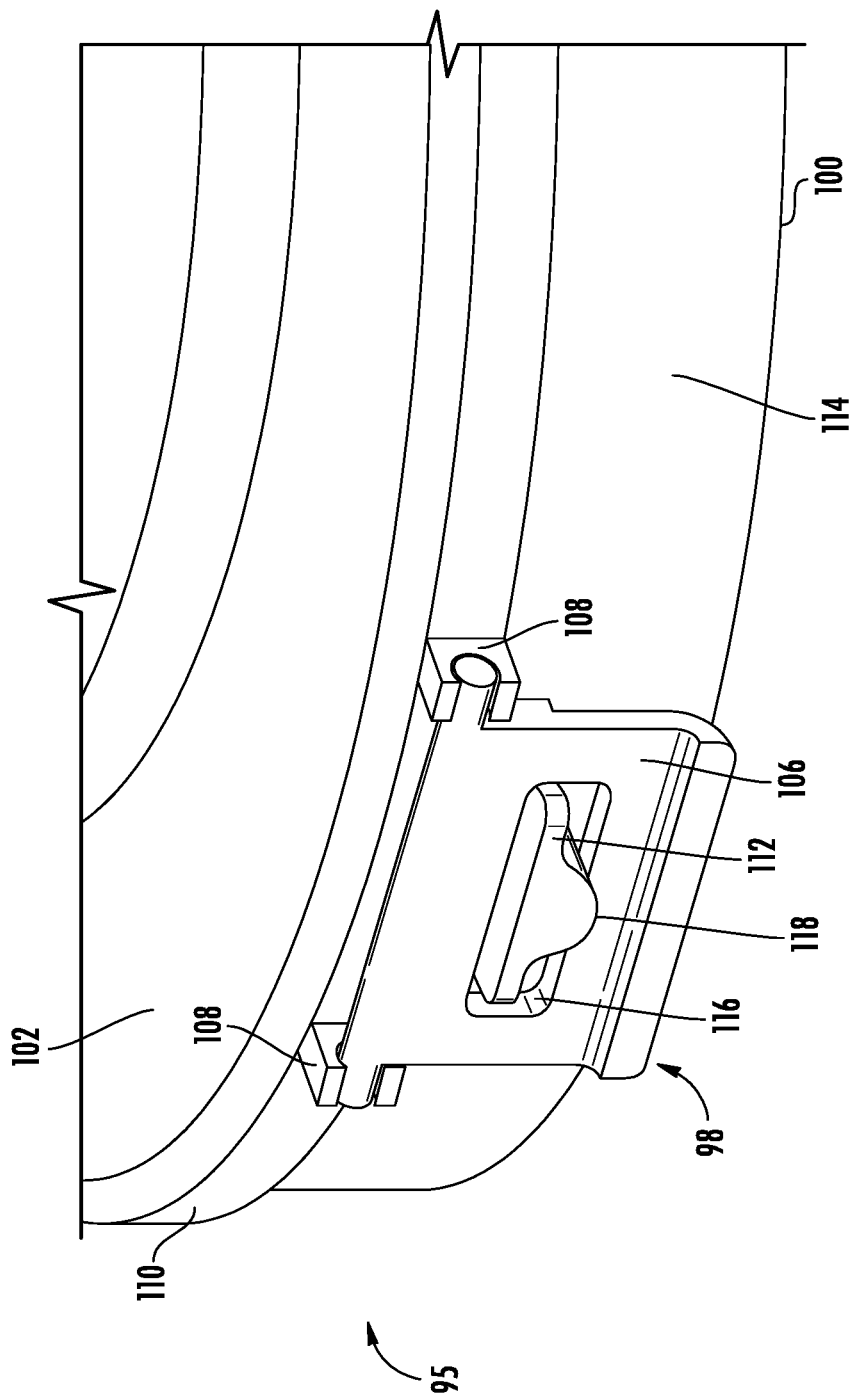
FIG. 15 shows a close-up view of a latch mechanism of the container of FIG. 13 in accordance with the present disclosure.

Referring now to FIGS. 13-15, a container 95 for a tissue cartridge 16 is shown. FIG. 13 shows a perspective view of an exemplary embodiment of a container 95, FIG. 14 shows a side view of the container 95 with a containment element 96 and positioning elements 97 and a pre-loaded tissue cartridge 16A therein, and FIG. 15 shows a close-up view of a latch mechanism 98 of the container. In one embodiment, the container 95 is sized and configured to receive and retain a pre-loaded tissue cartridge 16A (that is, a tissue cartridge 16 with graft tissue therein) and an amount of storage solution. Further, in one embodiment, the container 95 is a single-use container that, once opened, cannot be resealed (using the latch mechanism). In another embodiment, the container 95 is a multi-use container that can be opened and resealed many times. In some embodiments, the container 95, with a pre-loaded tissue cartridge 16A, and the injector 10 are sold together as a kit 99 (for example, as shown in FIG. 14). In other embodiments, the container 95, with or without a pre-loaded tissue cartridge 16, is sold separately from the injector 10.

Referring now to FIG. 14, in one embodiment, the container 95 generally includes a reservoir portion 100, a lid 102, and at least one latch mechanism 98 configured to couple the lid 102 to the reservoir portion 100. The reservoir portion 100 and the lid 102 together define a chamber 104 within the container 95 that is sized and configured to hold the tissue cartridge 16 and, optionally, a volume of preservation solution. In one embodiment, the container 95 also includes at least one containment element 96 configured to physically block the first opening 66 of the tissue cartridge 16A to prevent the graft tissue from escaping the tissue cartridge 16A during storage, shipping, and the like, and at least one positioning element (for example, positioning elements 97A-C shown in FIG. 14) configured to be in contact with and secure the tissue cartridge 16A within the container 95. The containment element(s) 96 and the positioning elements 97A-97C are not shown in FIG. 13 for clarity, but it will be understood that the container 95 of FIG. 13 may also include these elements. Alternatively, in some embodiments, the container 95 may not include containment and/or positioning elements.

Continuing to refer to FIG. 14, in one embodiment, the first positioning element 97A extends downward from an inner surface of (and is fixedly coupled to or integrated with) the lid 102 toward the floor of the reservoir portion 100, and the second positioning element 97B extends upward from (and is fixedly coupled to or integrated with) the floor of the reservoir portion 100 toward the lid 102 (that is, the first and second positioning elements 97A, 97B extend in opposite directions toward the tissue cartridge 16A). In one non-limiting example, each of the first and second positioning elements 97A, 97B includes a free end with a contoured or cutaway portion that sized and configured to retain at least a portion of the second portion 62 of the tissue cartridge 16A and/or the cap 70. In one non-limiting example, the third positioning element 97C extends upward from (and is fixedly coupled to or integrated with) the floor of the reservoir portion 100 toward the lid 102 and includes a free end with a contoured or cutaway portion that sized and configured to retain at least a portion of the first portion 60 of the tissue cartridge 16A. Thus, the tissue cartridge 16A is secured in place between the positioning elements 97A-97C within the chamber 104, and is prevented from shifting or moving, when the container 95 is closed, with the lid 102 secured to the reservoir portion 100. In one embodiment, the containment element 96 extends downward from an inner surface of (and is fixedly coupled to or integrated with) the lid 102 toward the floor of the reservoir portion 100 and is sized and shaped to block or obstruct at least a portion of the first opening 66 of the tissue cartridge 16A. In one embodiment, the containment element 96 is sized and shaped to obstruct at least a portion of the first opening 66 of the tissue cartridge 16A that is sufficient to prevent the graft tissue from escaping the tissue cartridge 16A and into the chamber 104. Likewise, a cap 70 may be coupled to the second portion 62 of the tissue cartridge 16A that obstructs the second opening 68 and prevents the graft tissue from escaping the tissue cartridge 16A and into the chamber 104 or out of the tissue cartridge 16A once the tissue cartridge 16A is removed from the container 95 and coupled to the injector 10, at least until the user is ready to deliver the graft tissue to the delivery site. Additionally, when the container 95 is opened, the first positioning element 97A and the containment element 96 are lifted away from the tissue cartridge 16A with the lid 102. However, the second and third positioning elements 97B, 97C maintain the position of the tissue cartridge 16A. The connection extension 34 of the injector 10 can then be inserted into the first opening 66 of the tissue cartridge 16A, without disrupting the tissue cartridge 16A and while the cap 70 maintains obstruction of the second opening 68 to keep the graft tissue within the chamber 64 of the tissue cartridge 16A. The cap 70 may remain on the tissue cartridge 16A until the user is ready to deliver the graft tissue to the delivery site. However, in other embodiments, the container 95 includes a second containment element that is sized and configured to obstruct at least a portion of the first opening 68. Further, it will be understood that the positioning elements 97A-97C and/or the at least one containment element 96 may have other sizes, shapes, and configurations other than those shown. For example, in some embodiments the positioning elements 97A-97C and/or the at least one containment element 96 may extend into the chamber 104 from locations on inner surfaces of the container 95 other than those shown and described, such as from a side wall of the reservoir portion 100, from the inner surface of the lid 102 rather than the floor of the reservoir portion 100, or the like.

Referring now to FIG. 15, in one embodiment, the latch mechanism 98 includes a latch 106 that is hingedly connected to clip elements 108 extending from an edge 110 of the lid 102, and a tab 112 that extends orthogonally from the side wall 114 of the reservoir portion 100. In one embodiment, the latch 106 includes an opening 116 that is sized and configured to accept at least a portion of the tab 112, and the tab 112 includes a protrusion 118 extending downward from the tab 112 and away from the lid. Thus, when the tab 112 extends through the opening 116 of the latch 106 far enough that the protrusion 118 also passes through the opening 116, the protrusion 118 holds the latch 106 in place to secure the lid 102 to the reservoir portion 100. Put another way, the latch 106 is configured to be securably snapped onto the tab 112. However, it will be understood that coupling elements other than the latch mechanism 98 shown in FIGS. 13 and 14 may be used, such as a clamp, a clasp, a tab and groove, a snap, or other suitable mechanism. Further, in some embodiments, words, symbols, or other indicia may be printed, etched, integrally molded with, or otherwise displayed on the lid 102, reservoir portion 100, or other portion of the container. In one non-limiting example, the lid 102 may be molded with words "single use only" in relief; however, it will be understood that any text or indicia may be used.

Figure 16:
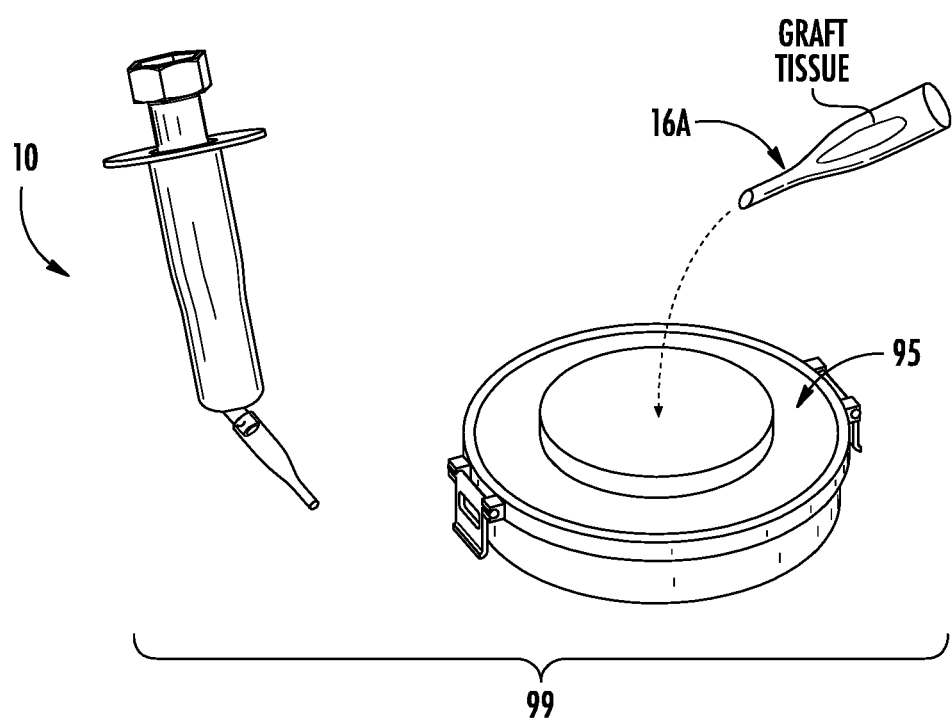
FIG. 16 shows a stylized view of an exemplary kit including a graft tissue injector and a container having a pre-loaded tissue cartridge therein, in accordance with the present disclosure.

Referring now to FIG. 16, an exemplary kit is shown, such as a kit for performing corneal transplant. In one embodiment, the kit 99 includes a container 95 with a pre-loaded tissue cartridge 16A therein, and an injector 10. However, it will be understood that the kit 99 may, in some embodiments, include additional components and/or a tissue cartridge 16A that is not pre-loaded (that is, a tissue cartridge 16 that does not include graft tissue therein at the time of sale).

Figure 17:
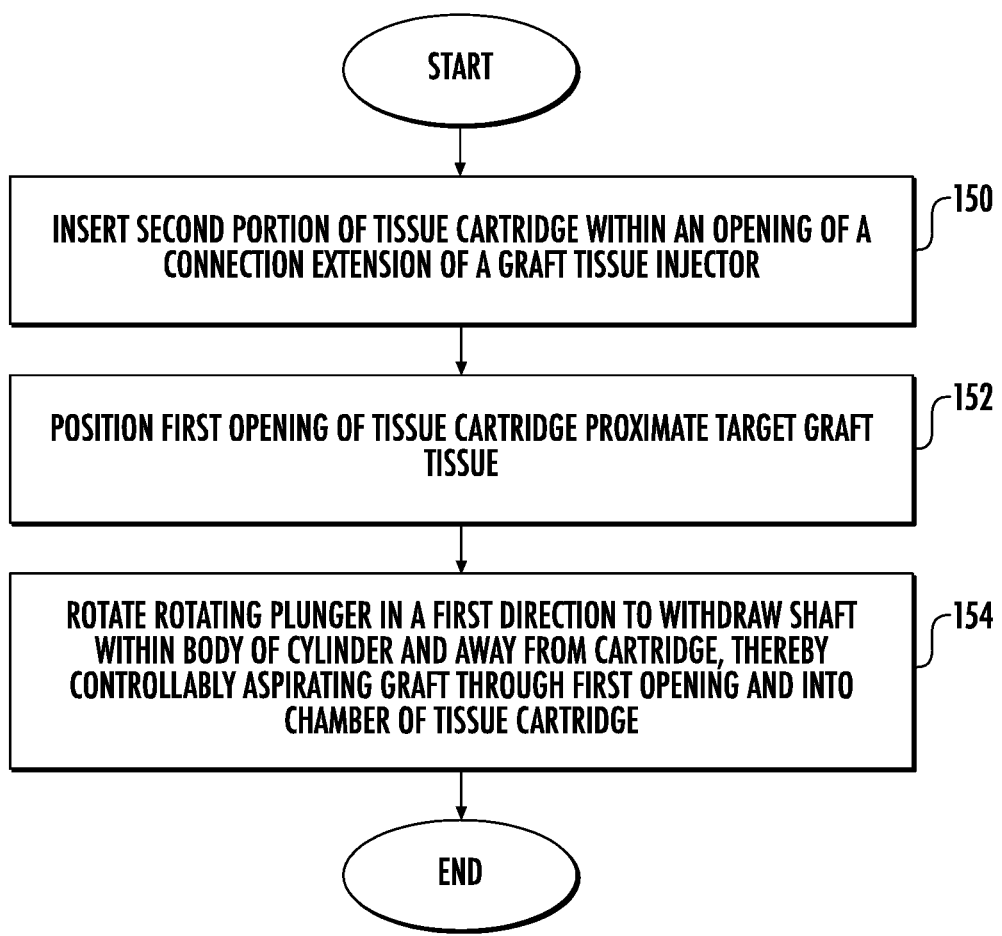
FIG. 17 shows an exemplary method of aspirating graft tissue into a graft tissue injector in accordance with the present disclosure.
Figure 18:
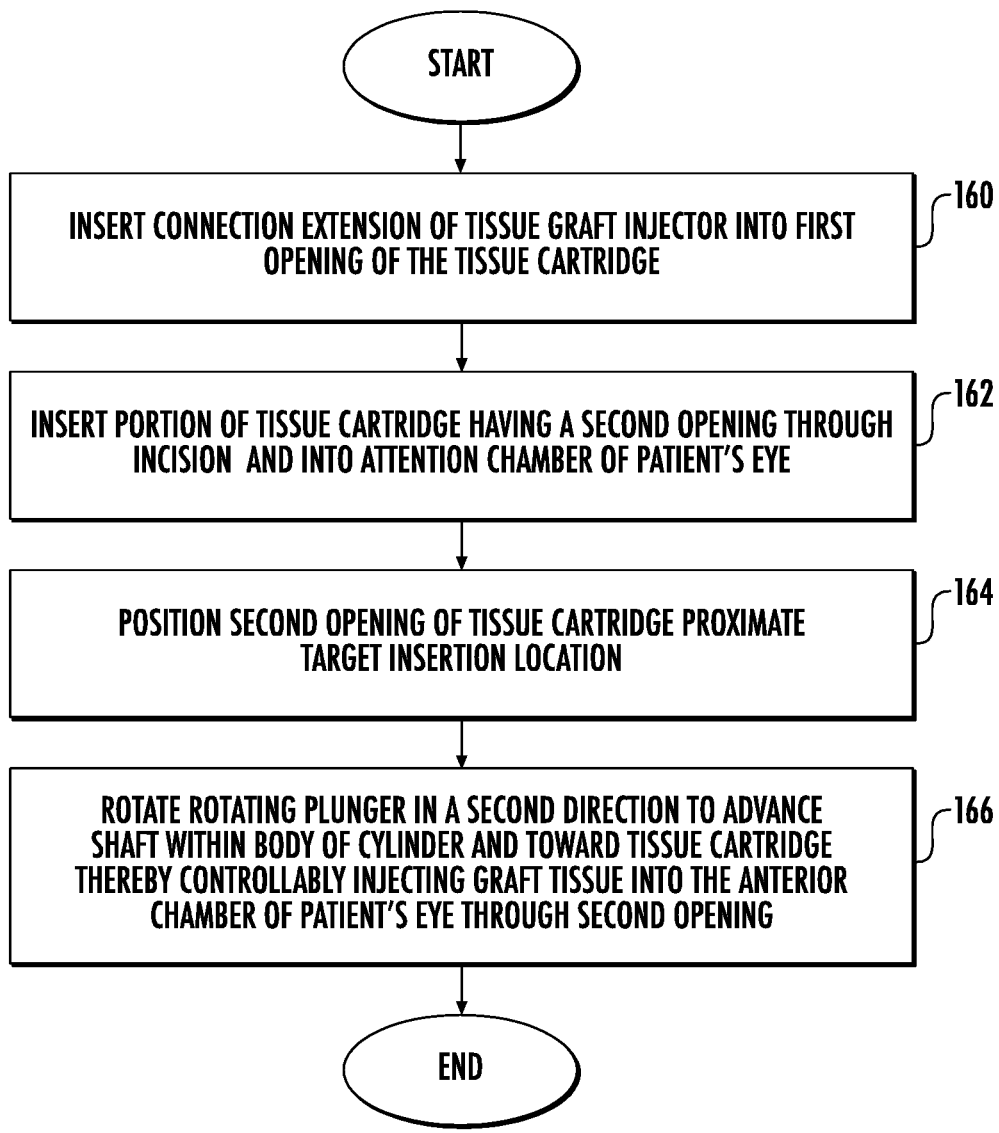
FIG. 18 shows an exemplary method of injecting graft tissue from a graft tissue injector in accordance with the present disclosure.

Referring now to FIGS. 17 and 18, an exemplary method of delivering graft tissue to a delivery site is shown. In one embodiment, the method may include aspirating graft tissue into an injector 10 (as shown in FIG. 17) and then delivering or injecting the graft tissue from the injector 10 into or at the delivery site (as shown in FIG. 18). In another embodiment, such as when the injector 10 is used with a pre-loaded tissue cartridge 16A, the method may include only delivering or injecting the graft tissue from the injector 10 into or at the delivery site (as shown in FIG. 18).

Referring now to FIG. 17, an exemplary method of aspirating a graft tissue with the injector 10 is shown. The graft tissue may be contained within a volume of suitable solution, such as balanced saline solution (BSS) or similar fluid. In use, the injector 10 may be partially filled with a solution suitable for containing the graft tissue without damage, such as BSS. Further, before aspirating the graft tissue, the user ensures the plunger 12 is in a position such that the shaft 20 may be further retracted within the chamber 40 in a direction away from the tissue cartridge 16. That is, the shaft 20 must be retracted within the chamber 40 in a direction opposite the tissue cartridge 16 at least over a distance sufficient to aspirate the graft tissue. In one non-limiting example, the user ensures the shaft 20 is fully advanced within the chamber 40 of the body 32 such that the free end 26 of the shaft 20 is in contact with an inner surface of the end wall 50 and/or that the rotating plunger 12 cannot be further advanced within the chamber 40 by rotating the knob in a first or clockwise direction. However, it will be understood that in some examples the shaft 20 is less than fully advanced.

Continuing to refer to FIG. 17, in a first step 150 the user engages the tissue cartridge 16 with the connection extension 34 of the cylinder 14 in a first or aspiration configuration. In one embodiment, the user inserts at least a portion of the second portion 62 of the tissue cartridge 16 into the opening 58 of the connection extension 34, thereby leaving the first portion 60, and the first opening 66, of the of the tissue cartridge 16 available for aspirating fluid and graft tissue into the chamber 64 of the tissue cartridge 16 (for example, as shown in FIG. 3). The first opening 66 is wider than the second opening 68, which may reduce the likelihood of graft tissue damage during aspiration.

Continuing to refer to FIG. 17, in a second step 152 the user positions the first opening 66 of the tissue cartridge 16 proximate the graft tissue. In one embodiment, the graft tissue is a narrow, elongate Descemet's roll formed spontaneously after a circular layer of endothelium/Descemet's membrane is removed from the donor posterior stroma, and is stained with blue stain such as 0.06% trypan blue. To aspirate the graft tissue through the first opening 66 and into the chamber 64 in a third step 154, in one embodiment (for example, using the injector 10 of FIGS. 1-4) the user slowly rotates the knob 19 of the plunger 12 in a second direction opposite the first direction (for example, the counter-clockwise direction). Rotation of the knob 19 in the second direction retracts the shaft 20 within the chamber 40 of the body 32 in a direction that is away from the tissue cartridge 16, which in turn draws in the solution in which the graft tissue is located (for example, BSS), as well as the graft tissue. In another embodiment (for example, using the injector 10 of FIGS. 9-11), the user retracts the plunger 12 longitudinally (that is, linearly along the first longitudinal axis 17 of the cylinder 14 without rotation) in a direction that is away from the tissue cartridge 16, which in turn draws in the solution in which the graft tissue is located (for example, BSS), as well as the graft tissue. In one embodiment, the first opening 66 of the tissue cartridge 16 is sized and configured such that the graft tissue may pass without resistance through the first opening 66 and into the chamber 64. Thus, upon aspiration of the graft tissue, the graft tissue is located within the chamber 64 of the tissue cartridge 16 within BSS or similar fluid. The plunger 12 allows the user to aspirate the graft tissue more slowly and with more precision and control than offered by currently known syringe-type injectors.

Referring now to FIG. 18, an exemplary method of injecting graft tissue from the injector 10 is shown. In some embodiments, the method of FIG. 18 begins after the method of FIG. 17 is performed. In other embodiments, such as when the injector 10 is used with a pre-loaded tissue cartridge 16A (such as is discussed above regarding FIGS. 13-15), the user may simply begin the method of FIG. 18 by using the pre-loaded tissue cartridge 16A. In any embodiment, in a first step 160, the user engages the tissue cartridge 16 with the connection extension 34 of the cylinder 14 in a second or injection configuration. In one embodiment, the user inserts at least a portion of the connection extension 34 into the first opening 66 of the tissue cartridge 16, thereby leaving the second portion 62, and the second opening 68, of the tissue cartridge 16 free to insert into the patient's eye and deliver or inject the graft tissue (as shown in FIGS. 1 and 2).

Continuing to refer to FIG. 18, in a second step 162, at least a portion of the second portion 62 of the tissue cartridge 16 (that is, the narrow tip of the tissue cartridge 16) is inserted through an incision, such as a scleral or corneal incision, and into the anterior chamber of the patient's eye. In a third step 164, the second opening 68 of the tissue cartridge 16 is positioned at a target delivery site within the anterior chamber. In a fourth step 166, in one embodiment (for example, using the injector 10 of FIGS. 1-4) the user slowly rotates the knob 19 of the plunger 12 in the first direction (for example, the clockwise direction), which advances the shaft 20 within the chamber 40 of the body 32 in a direction that is toward the tissue cartridge 16, which in turn ejects the fluid (for example, BSS) and the graft tissue from the tissue cartridge 16 and into the anterior chamber of the patient's eye. In another embodiment (for example, using the injector 10 of FIGS. 7-9), the user rotates the plunger 12 in a direction, such as clockwise, to advance the shaft 20 in a direction toward the tissue cartridge 16, which ejects fluid and the graft tissue from the tissue cartridge 16 and into the anterior chamber of the patient's eye. Further, the narrow diameter of the chamber 64 within the second portion 62 of the tissue cartridge 16 may help align the graft tissue in the proper orientation for delivery to the target delivery site. Rotating the plunger 12 to advance the plunger 12 allows the user to inject the graft tissue into the anterior chamber more slowly and with more precision and control than offered by currently known syringe-type injectors. Additionally, injecting the graft tissue and fluid more slowly into the anterior chamber may help prevent over-pressurization of the anterior chamber during delivery.

Other embodiments may include:

Embodiment 1

An injector comprising: a cylinder; and a plunger at least partially located within the cylinder, the plunger being rotatably and longitudinally advanceable within the cylinder.

Embodiment 2

The injector of Embodiment 1, wherein rotating the plunger in a first direction within the cylinder controllably aspirates a graft tissue into the injector and rotating the plunger in a second direction opposite the first direction controllably ejects the graft tissue from the injector.

Embodiment 3

The injector of Embodiment 1, wherein the cylinder includes a body having: a first portion defining a first opening; a second portion opposite the first portion, the second portion defining a second opening; and a chamber, the chamber being in fluid communication with the first opening and the second opening.

Embodiment 4

The injector of Embodiment 3, wherein the chamber has a first diameter within the first portion of the body and the chamber has a second diameter within the second portion of the body, the first diameter being greater than the second diameter.

Embodiment 5

The injector of Embodiment 3, wherein the cylinder further includes a connection extension having: a first end coupled to the second portion of the body; a second end opposite the first end, the second end defining an opening;

and a lumen, the lumen being in fluid communication with the second opening of the body and the second opening of the connection extension.

Embodiment 6

The injector of Embodiment 5, wherein the body has a first longitudinal axis and the connection extension has a second longitudinal axis that is different than the first longitudinal axis.

Embodiment 7

The injector of Embodiment 6, wherein the second longitudinal axis is oriented at an angle from the first longitudinal axis, the angle being between approximately 22.5° and approximately 67.5°.

Embodiment 8

The injector of Embodiment 5, wherein the plunger includes: a shaft having a first portion and a second portion opposite the first portion, the second portion having a free end; and a knob coupled to the first portion of the shaft, an outer surface of at least a portion of the first portion of the shaft being threaded.

Embodiment 9

The injector of Embodiment 8, wherein at least a portion of an inner surface of the body within the chamber is threaded, the threaded portion of the shaft of the plunger being mateably engageable with the threaded portion of the inner surface of the body.

Embodiment 10

The injector of Embodiment 5, further comprising a tissue cartridge including: a first portion defining a first opening and having a first outer diameter; a second portion opposite the first portion and defining a second opening, the second portion having a second outer diameter that is less than the first outer diameter; and a chamber, the chamber being in fluid communication with the first opening of the tissue cartridge and the second opening of the tissue cartridge.

Embodiment 11

The injector of Embodiment 10, wherein the first opening of the tissue cartridge has a first diameter and the second opening of the tissue cartridge has a second diameter that is less than the first diameter.

Embodiment 12

The injector of Embodiment 11, wherein: the connection extension has an outer diameter that is slightly smaller than the diameter of the first opening of the tissue cartridge, such that the connection extension is removably insertable within the first opening of the tissue cartridge and securable therein by friction fit; and the connection extension has an inner diameter that is slightly larger than the outer diameter of the second portion of the tissue cartridge, such that the second portion of the tissue cartridge is removably insertable within the connection extension and securable therein by friction fit.

Embodiment 13

The injector of Embodiment 10, wherein the tissue cartridge is composed of polymer.

Embodiment 14

The injector of Embodiment 13, wherein the body is composed of a material from the group consisting of plastic, glass, and polymer.

Embodiment 15

The injector of Embodiment 10, wherein at least a portion of the tissue cartridge is coated with at least one layer of a lubricious material.

Embodiment 16

The injector of Embodiment 15, wherein both an outer surface and an inner surface within the chamber of the second portion of the tissue cartridge are coated with the at least one layer of nano-ceramic material.

It should be understood that various aspects disclosed herein may be combined in different combinations than the combinations specifically presented in the description and the accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, delivery of corneal graft tissue to a delivery site.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention.

What is claimed is:
1. An injector comprising:
   a cylinder, the cylinder including;
      a body having a first end, a second end opposite the first end, and a chamber extending therebetween; and
      a connection extension, the connection extension extending directly from the second end of the body, the connection extension and the body being formed as a single, unitary piece, the connection extension having a first end meeting the second end of the body, a second end opposite the first end, and a lumen extending therebetween that is in fluid communication with the chamber of the body, at least the first end of the connection extension having an outer diameter that is less than a diameter of the chamber of the body; and
   a plunger at least partially located within the cylinder, the plunger being rotatably advanceable and rotatably retractable within the cylinder,
   the body having a first longitudinal axis extending from the first end of the body to the second end of the body and the connection extension having a second longitudinal axis extending from the first end of the connection extension to the second end of the connection extension, the second longitudinal axis being oriented at an acute angle from the first longitudinal axis, such that the second longitudinal axis at the second end of the connection extension is oriented at an acute angle to the first longitudinal axis at the second end of the body.

2. The injector of claim 1, wherein rotating the plunger in a first direction within the cylinder is configured to controllably aspirate a graft tissue into the injector and rotating the plunger in a second direction opposite the first direction is configured to controllably eject the graft tissue from the injector.

3. The injector of claim 2, wherein the plunger includes:
a shaft having a first portion and a second portion opposite the first portion, the second portion having a free end; and
a knob coupled to the first portion,
an outer surface of at least a portion of the first portion defining threading.

4. The injector of claim 3, wherein:
the body of the cylinder has an inner surface, at least a portion of the inner surface defining threading that is complementary to the threading of the first portion of the outer surface of the shaft of the plunger.

5. The injector of claim 1, wherein the body of the cylinder has:
a first opening at the first end; and
a second opening at the second end
the chamber of the body being in fluid communication with the first opening of the body and the second opening of the body.

6. The injector of claim 5, wherein the body of the cylinder further includes an end wall at least partially defining the second opening, the connection extension extending from the end wall, the lumen of the connection extension being in fluid communication with the second opening of the body, the outer diameter of the connection extension at at least the first end of the connection extension being less than a diameter of the end wall.

7. The injector of claim 1, wherein the angle at which the second longitudinal axis is oriented from the first longitudinal axis is between approximately 22.5° and approximately 67.5°.

8. The injector of claim 1, further comprising a tissue cartridge including:
a first portion defining a first opening and having a first outer diameter, the first opening having a first diameter;
a second portion opposite the first portion and defining a second opening, the second portion having a second outer diameter that is less than the first outer diameter of the first portion and the second opening having a second diameter that is less than the first diameter of the first opening; and
a chamber, the chamber being in fluid communication with the first opening of the tissue cartridge and the second opening of the tissue cartridge.

9. The injector of claim 8, wherein:
the connection extension has an outer diameter that is slightly smaller than the first diameter of the first opening of the tissue cartridge, such that the connection extension is removably insertable within the first opening of the tissue cartridge and securable therein by friction fit; and
the connection extension has an inner diameter that is slightly larger than the outer diameter of the second portion of the tissue cartridge, such that the second portion of the tissue cartridge is removably insertable within the connection extension and securable therein by friction fit.

10. The injector of claim 8, wherein the tissue cartridge further includes an inner surface and an outer surface, at least a portion of at least one of the inner surface and the outer surface being coated with at least one layer of a nano-ceramic material.

* * * * *